United States Patent
Paolicchi et al.

(10) Patent No.: US 10,605,803 B2
(45) Date of Patent: Mar. 31, 2020

(54) COMPOSITION FOR ENZYME IMMUNOASSAY USING IMMUNOFLUORESCENCE AND USES THEREOF

(71) Applicant: BIOMERIEUX, Marcy L'Etoile (FR)

(72) Inventors: Aldo Paolicchi, Pisa (IT); Antonio Sanesi, Florence (IT); Veronica Lucia Rossi, Arezzo (IT); Andrea Ienco, Sesto Fiorentino (IT); Vanessa Susini, Cascina (IT)

(73) Assignee: BIOMERIEUX, Marcy l'Etoile (FR)

( * ) Notice: Subject to any disclaimer, the term of this patent is extended or adjusted under 35 U.S.C. 154(b) by 80 days.

(21) Appl. No.: 15/519,708

(22) PCT Filed: Oct. 16, 2015

(86) PCT No.: PCT/FR2015/052779
§ 371 (c)(1),
(2) Date: Apr. 17, 2017

(87) PCT Pub. No.: WO2016/059351
PCT Pub. Date: Apr. 21, 2016

(65) Prior Publication Data
US 2017/0241994 A1   Aug. 24, 2017

(30) Foreign Application Priority Data
Oct. 17, 2014 (FR) ..................... 14 60003

(51) Int. Cl.
*G01N 33/542* (2006.01)
*G01N 33/533* (2006.01)
*G01N 33/543* (2006.01)
*G01N 33/58* (2006.01)

(52) U.S. Cl.
CPC ......... *G01N 33/542* (2013.01); *G01N 33/533* (2013.01); *G01N 33/54393* (2013.01); *G01N 33/581* (2013.01)

(58) Field of Classification Search
CPC ........................... G01N 33/542; G01N 33/533
See application file for complete search history.

(56) References Cited

U.S. PATENT DOCUMENTS

| | | |
|---|---|---|
| 3,551,295 A | 12/1970 | Dyer |
| 5,854,008 A | 12/1998 | Diamandis |

(Continued)

OTHER PUBLICATIONS

Susini et al. ("Fluorescence enhancement aided by metal ion displacement", Biosensors and Bioelectronics, vol. 80, pp. 237-242, published 2016) (Year: 2016).*

(Continued)

*Primary Examiner* — Tracy Vivlemore
*Assistant Examiner* — Nam P Nguyen
(74) *Attorney, Agent, or Firm* — Oliff PLC

(57) ABSTRACT

A composition for enzyme immunoassay using immunofluorescence comprises (i) a fluorogenic enzymatic substrate and (ii) a quenched fluorogenic compound that forms a fluorescent compound after hydrolysis of the fluorogenic enzymatic substrate. The composition may be useful for performing a method for in vitro detection and/or quantification of an analyte of a liquid test sample liable to contain the analyte.

18 Claims, 6 Drawing Sheets

(56) References Cited

U.S. PATENT DOCUMENTS

Figure 1:

| | | | |
|---|---|---|---|
| 7,592,182 B2* | 9/2009 | Milne | G01N 33/68 436/161 |
| 2007/0111222 A1* | 5/2007 | Chasin | A61K 38/28 435/6.11 |

OTHER PUBLICATIONS

Seto et al. ("A simple and selective fluorometric assay for dopamine using a calcein blue-Fe2+ complex fluorophore", Talanta, vol. 94, pp. 36-43, published Mar. 8, 2012). (Year: 2012).*

ThermoFisher (Overview of ELISA, print retrieved Apr. 2019) (Year: 2019).*

Álvaro et al., "A bis-benzimidazole-derived N, S macrocycle as sensor for transition metal ions in aqueous solution," Chemical Physics Letters, Dec. 21, 2001, vol. 350, pp. 240-246.

Henary et al., "Zin(II)-Selective Ratiometric Fluorescent Sensors Based on Inhibition of Excited-State Intramolecular Proton Transfer," Chem. Eur. J., 2004, vol. 10, pp. 3015-3025.

Jung et al., "Coumarin-Derived Cu2+-Selective Fluorescence Sensor: Synthesis, Mechanisms, and Applications in Living Cells," Journal of American Chemical Society, 2009, vol. 131, pp. 2008-2012.

Leong et al., "Self-Assembly of Ion-Pair Complexes," Crystal Growth & Design, 2007, vol. 7, No. 10, pp. 2112-2116.

Rassaie et al., "Influence of different combinations of antibodies and penicillinase-labeled testosterone derivatives on sensitivity and specificity of immunoassays," Steroids, 1992, vol. 57, pp. 112-118.

Saluja et al., "A benzimidazole-based fluorescent sensor for Cu2+ and its complex with a phosphate anion formed through a Cu2+ displacement approach," Tetrahedron Letters, 2012, vol. 53, pp. 3292-3295.

Stabler et al., "Chemiluminescence Immunoassay of Aldosterone in Serum," Clinical Chemistry, 1991, vol. 37, No. 11, pp. 1987-1989.

Thomas et al., "Calcein as a Fluorescent Probe for Ferric Iron," The Journal of Biological Chemistry, May 7, 1999, vol. 274, No. 19, pp. 13375-13383.

Yao et al., "A new coumarin-based chemosensor for Fe3+ in water," Inorganic Chemistry Communications, 2009, vol. 12, pp. 116-118.

Zhang et al., "Facile fabrication of a cost-effective, water-soluble, and electrosynthesized poly(9-aminofluorene) fluorescent sensor for the selective and sensitive detection of Fe(III) and inorganic phosphates," Sensors and Actuators B: Chemical, 2012, vol. 171-172, pp. 786-794.

Jan. 29, 2016 International Search Report issued in International Patent Application No. PCT/FR2015/052779.

* cited by examiner

COMPOSITION FOR ENZYME IMMUNOASSAY USING IMMUNOFLUORESCENCE AND USES THEREOF

The present invention relates to a composition for enzyme immunoassay using immunofluorescence, a kit and an automated device for immunoanalyses containing such a composition, and also an associated method for in vitro detection and/or quantification of an analyte of interest by enzyme immunoassay using immunofluorescence.

Detection methods using immunoassay are widely used in the field of diagnostics. These methods make it possible to detect analytes in test samples, especially in the form of proteins (antigens/antibodies), peptides and haptens, such as, for example, steroids or vitamins. Immunoassay is a method widely known to those skilled in the art, involving immunological reactions between the analyte to be detected and one or more binding partners to this analyte.

The results of immunoassays are then supplied by a laboratory to a practitioner who will interpret them in order, for example, to diagnose a pathological condition or else the presence of undesirable microorganisms, and then take the necessary measures, for example giving an appropriate treatment to the patient or decontaminating an industrial environment containing these undesirable microorganisms. It is therefore particularly important for these assays to be both highly sensitive, in the sense that they do not give false negatives, and highly specific, in the sense that they do not give false positives.

Enzyme immunoassays or EIA constitute a type of immunoassay widely used in the field of analysis of samples liable to contain analytes of interest. These assays are coupled to a reaction catalyzed by an enzyme, using an enzymatic substrate. Depending on the enzymatic substrate chosen, there may be a colorimetric signal (ELISA, for *Enzyme-Linked Immunosorbent Assay*) (Rassasie, M. J., et al., 1992), a fluorescence signal (ELFA technology, for Enzyme Linked Fluorescence Assay) or a chemiluminescent signal (CLIA, for *Chemiluminescence Immuno Assays*) (Stabler T. V., et al., 1991).

These methods are based on measurements making it possible to quantify the signals emitted during the analysis of the test sample. The amount of signal detected is generally proportional to the amount of analyte to measure (for example during a sandwich assay) or inversely proportional to the amount of analyte to measure (for example competitive assay).

The "ELFA" technology, which makes it possible to quantify fluorescence signals and to obtain more sensitive results, uses an enzyme which converts a fluorogenic enzymatic substrate into a fluorescent reaction product, and optionally into one or more other reaction products, according to the general equation (1) well known to those skilled in the art:

$$E+S \rightarrow ES \rightarrow E+S^* \quad (1)$$

in which "E" is enzyme, "S" is fluorogenic enzymatic substrate, "ES" corresponds to the enzyme-substrate complex and "S*" corresponds to a fluorescent reaction product resulting from the fluorogenic enzymatic substrate.

The reaction product S* contained in the reaction medium becomes fluorescent when it is excited by light of a particular wavelength.

Indeed, applying the principle of fluorescence, the reaction product exposed to or excited by a light source corresponding to a first wavelength will in turn emit light rays or fluorescence signals at a second wavelength. The first, excitation, wavelength generally varies in a range from 250 to 450 nm. The second, emission, wavelength, for its part, is located in an emission range located between 300 and 600 nm.

Thus, the detection of fluorescence signals (in relative fluorescence units) combined with a treatment of the signal of these fluorescence signals originating from the reaction medium, itself originating from the sample to be tested and containing the reaction products, makes it possible to determine, for example, the presence or the concentration of the analyte of interest sought within the sample.

Nonetheless, even if the ELFA technology is more sensitive than ELISA colorimetric assays, those skilled in the art are still seeking solutions which make it possible to further improve signal detection. This is because fluorimetric measurements are subject to problems which non-specifically decrease or increase the signal output.

Thus, the detection of fluorescence may vary as a function of parameters such as pH, temperature, ionic concentration, dryness, the presence of interference associated with the sample tested or else the solid matrix. These parameters especially influence light scattering and background noise, which affects the sensitivity of an assay, especially using fluorescence ("*Selecting the Detection System—Colorimetric, Fluorescent, Luminescent Methods*" (Gibbs et al., Elisa Technical Bulletin No. 5, 2001).

In light of the above, there is currently a need to find novel means or alternative means which make it possible to increase both the specificity and the sensitivity of the ELFA technology.

Thus, a technical problem which the present invention aims to solve is to make enzyme immunoassays using immunofluorescence more effective and more rapid, and in particular to increase the sensitivity, that is to say to increase the ability to give a positive result when a hypothesis is verified, especially when the analyte is present in the test sample in a small amount.

The first subject of the solution proposed by the invention to this problem is a composition for enzyme immunoassay using immunofluorescence comprising (i) a fluorogenic enzymatic substrate and (ii) a quenched fluorogenic compound forming a fluorescent compound after hydrolysis of the fluorogenic enzymatic substrate (i).

More particularly, this composition according to the invention comprises or consists of:
  on the one hand, a fluorogenic enzymatic substrate enabling, after enzymatic hydrolysis, the formation of a fluorescent product and of a second reaction product which is preferentially an anion; and
  on the other hand, a quenched fluorogenic compound enabling, after enzymatic hydrolysis of said fluorogenic enzymatic substrate and by virtue of the second reaction product released, the formation of a fluorescent compound resulting from the quenched fluorogenic compound.

Indeed, as indicated above, during an enzymatic reaction, the enzyme converts the fluorogenic enzymatic substrate into a fluorescent reaction product, but also gives rise to the formation of a second reaction product, generally considered to have no particular interest. The general equation (2) of such an enzymatic reaction may be written as follows:

$$E+S \rightarrow ES \rightarrow E+S^*+B \quad (2)$$

in which "E" is enzyme, "S" is fluorogenic enzymatic substrate and "ES" corresponds to the enzyme-substrate complex, "S*" corresponds to a fluorescent reaction product and "B" corresponds to a second reaction product, the two compounds "S*" and "B" being present in the reaction medium.

Surprisingly, the Applicant was able to demonstrate that it was possible to use the second, non-fluorescent, product "B" from the enzymatic reaction, to react it with a quenched fluorogenic compound "A". After reaction, the product "B" reacts directly or indirectly with the quenched fluorogenic compound "A", enabling the generation of a fluorescent product "A*" or "A*–B".

Direct reaction of the product "B" with the quenched fluorogenic compound "A" is intended to mean:
either that the product "B" reacts with the quenched fluorogenic compound "A" to release a fluorescent compound "A*" on the one hand, and a reaction product "B'", on the other hand, according to the following equation (3.i):

$$A+B \rightarrow A^*+B' \quad (3.i)$$

or the product "B" binds specifically to the quenched fluorogenic compound "A" to form a fluorescent compound "A*–B" associating the quenched fluorogenic compound "A" with the product "B" according to the following equation (3.ii):

$$A+B \rightarrow A^*-B \quad (3.ii)$$

The quenched fluorogenic compound preferably comprises a portion which will emit the fluorescence "A" and a releasable cation "cat", which is then read as "A-cat", and the general equation of the direct chemical reaction can be written as follows:

$$B+A\text{-cat} \rightarrow \text{cat-}B+A^* \quad (4)$$

in which "B" corresponds to the second reaction product detailed in the general equation (2) above, "A-cat" is the quenched fluorogenic compound comprising a portion which will be able to emit the fluorescence "A*" after releasing its cation "cat", which cation "cat" will associate with the product "B" to form a product "cat-B".

Indirect reaction of the product "B" with the quenched fluorogenic compound is intended to mean that the product "B" is used in a set of reactions making it possible to transform the quenched fluorogenic compound into a fluorescent compound, without binding of the product "B" to said quenched fluorogenic compound "A". The product "B" then binds to another compound present in the set of reactions, which will then be used in a step making it possible to make the quenched fluorogenic compound fluorescent.

Thus, in an innovative way, the Applicant uses the product "B", usually considered to be without interest, resulting from the enzymatic reaction detailed in equation (2) above, in order to increase the fluorescent signal, by reacting, in the reaction medium, said reaction product "B" with a quenched fluorogenic compound. By reusing reaction products which were a priori without interest, the Applicant thereby considerably increases the fluorescent signal.

This reuse of non-fluorescent reaction products especially has the following advantages:
it limits the addition of additional agents, the synthesis of which is complicated and difficult to reproduce, such as, for example, dendrimers used to amplify the signal, thereby making it possible to increase the sensitivity, the preparation of raw materials and the rapidity of the tests;
the increase in sensitivity obtained is achieved without changing the reaction time;
the additional reaction between the non-fluorescent reaction product and the quenched fluorogenic compound, in particular in the case of direct reaction between the reaction product "B" and said quenched fluorogenic compound is simple, rapid, and does not require many steps;
it does not require any modification of the instrument detecting the signal and is therefore generally relatively inexpensive;
it makes it possible to detect analytes present in low concentration in the test sample;
it makes it possible to adjust the concentrations of the quenched fluorogenic compound ("A-cat") to only increase the fluorescence of weak signals;
the fluorescence signals of the fluorescent reaction product ("S*") and of the quenched fluorogenic compound "A" or "A-cat" made fluorescent by virtue of the product "B" ("A*" or "A*–B") are detected within wavelength ranges located within the same interval.

A second subject of the invention is a kit for enzyme immunoassay using fluorescence comprising a composition according to the invention.

Its third subject is an automated device for immunoanalyses comprising a composition according to the invention.

Its fourth subject is the use of a composition, of a kit or of an automated device according to the invention, for enzyme immunoassay using immunofluorescence.

Its fifth subject is a method for in vitro detection and/or quantification of an analyte by enzyme immunoassay using immunofluorescence of sandwich type in a liquid test sample liable to contain said analyte, comprising or consisting in the following steps of:
bringing together a capture partner, attached or not attached beforehand to a solid surface, and said liquid sample for binding the analyte to the capture partner;
adding a detection partner, which is coupled directly or indirectly to an enzyme capable of lysing the fluorogenic enzymatic substrate of a composition of the invention, for binding to the capture partner-analyte complex;
bringing together a composition of the invention and the capture partner-analyte-detection partner complex to form a reaction medium; and
detecting, by immunofluorescence, the presence and/or the amount of analyte by measuring the fluorescence emitted in the reaction medium.

Its sixth subject is a method for in vitro detection and/or quantification of an analyte by enzyme immunoassay using immunofluorescence in a liquid test sample liable to contain said analyte, comprising or consisting in the following steps of:
bringing together a capture partner, attached or not attached beforehand to a solid surface, an analog of the analyte coupled to an enzyme able to lyse the fluorogenic enzymatic substrate of a composition of the invention, and said liquid sample, which compete to bind to the capture partner;
bringing together a composition of the invention and the capture partner-analyte and capture partner-analyte analog complexes to form a reaction medium; and
detecting, by immunofluorescence, the presence and/or amount of analyte by measuring the fluorescence emitted in the reaction medium.

Finally, its final subject is a method for improving the sensitivity of a method for in vitro detection and/or quantification, by enzyme immunoassay using immunofluorescence, of an analyte of interest in a test sample, characterized in that it comprises the use of a composition according to the invention while carrying out the assay.

Figure 2:
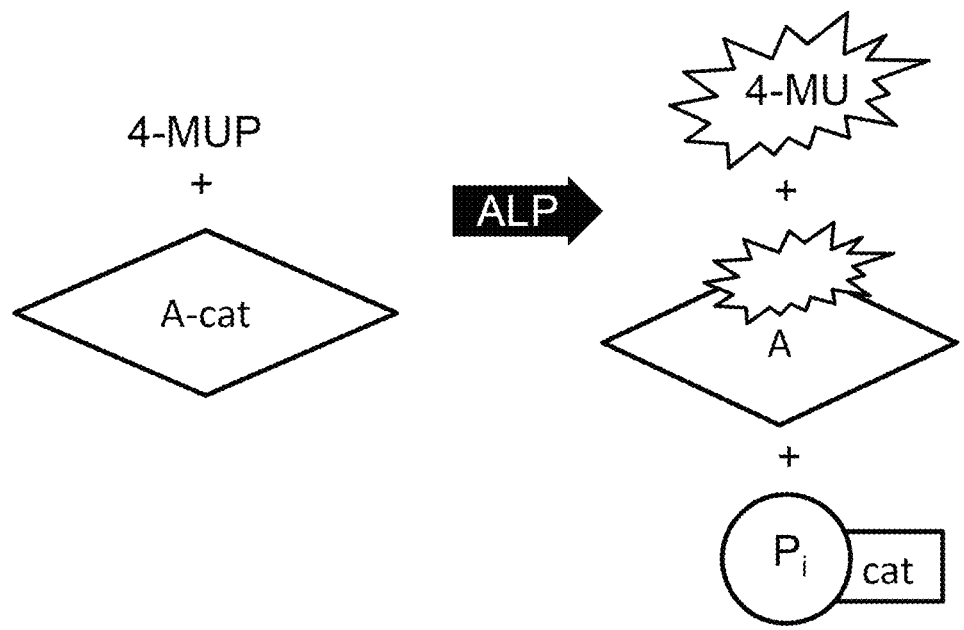
Figure 3:
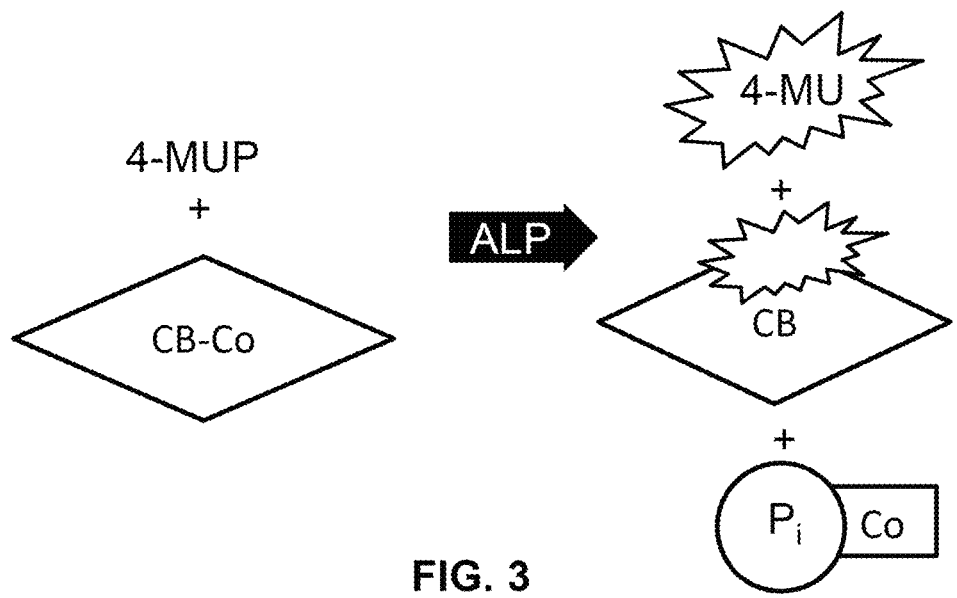
Figure 4:
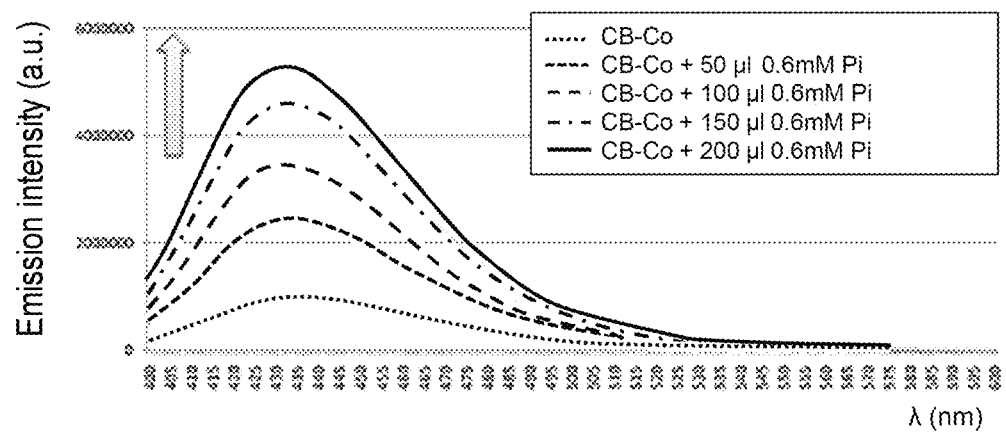
Figure 5:
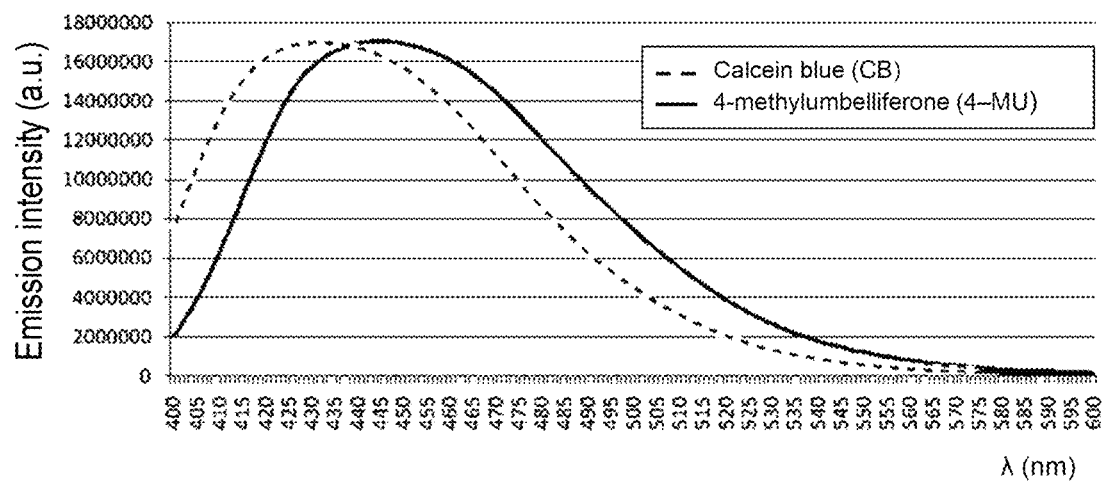

The invention will be better understood on reading the following nonlimiting description given in light of the appended drawings, in which:

FIG. 1 schematically represents a known reaction for activating a fluorogenic enzymatic substrate which is 4-methylumbelliferyl phosphate (4-MUP), to give 4-methylumbelliferone (4-MU) and a hydrogen phosphate ion $HPO_4^{2-}$ (Pi represents inorganic phosphate in all its forms), by the enzyme alkaline phosphatase (ALP);

FIG. 2 schematically represents a reaction for activating a fluorogenic enzymatic substrate, in this case 4-methylumbelliferyl phosphate (4-MUP), optimized by a quenched fluorogenic compound which is a quenched chemosensor-cation complex (A-cat); the substrate 4-MUP being converted by the enzyme alkaline phosphatase (ALP) to give 4-methylumbelliferone (4-MU) and a hydrogen phosphate ion $HPO_4^{2-}$ (Pi represents inorganic phosphate in all its forms), said resultant hydrogen phosphate ion $HPO_4^{2-}$ binding specifically to the cation of the quenched chemosensor-cation complex A-cat to form on the one hand a non-fluorescent product associating the cation with the phosphate ion (Pi-cat), and on the other hand a fluorescent compound (A*);

FIG. 3 schematically represents a specific reaction for activating the fluorogenic enzymatic substrate 4-methylumbelliferyl phosphate (4-MUP), optimized by the quenched chemosensor-cation complex which associates calcein blue and a cobalt ion ("CB-Co"); the substrate 4-MUP being converted by the enzyme alkaline phosphatase (ALP) to give 4-methylumbelliferone (4-MU) and a hydrogen phosphate ion $HPO_4^{2-}$ (Pi represents inorganic phosphate in all its forms), said resultant hydrogen phosphate ion $HPO_4^{2-}$ binding specifically to the cation of the quenched chemosensor-cation product which associates calcein blue and a cobalt ion ("CB-Co"), to form on the one hand a non-fluorescent product associating the cation with the phosphate ion (Pi-Co), and on the other hand to release the fluorescent compound calcein blue (CB*) the medium;

FIG. 4 illustrates that the quenched fluorogenic compound which is the quenched chemosensor-cation complex associating calcein blue and a cobalt ion ("CB-Co"), is activated by increasing concentrations of inorganic phosphate Pi and makes it possible to form the fluorescent compound calcein blue (CB*) as a function of said concentration of inorganic phosphate Pi [wavelength λ in nm/emission intensity in arbitrary units (a.u.)];

FIG. 5 illustrates that the emission spectrum of the two following solutions, measured using a spectrofluorometer, is substantially similar:
- a solution at pH 9.4 comprising 6410 nM of calcein blue, 0.6 mM of diethanolamine (DEA); 0.3 mM of ethylenediaminetetraacetic acid (EDTA) and 0.5 mM of $MgCl_2$; and
- a VIDAS® OPT solution which comprises 6410 nM of fluorogenic enzymatic substrate 4-methylumbelliferyl phosphate (4-MUP) [wavelength λ in nm/emission intensity in arbitrary units (a.u.)]

Figure 6:
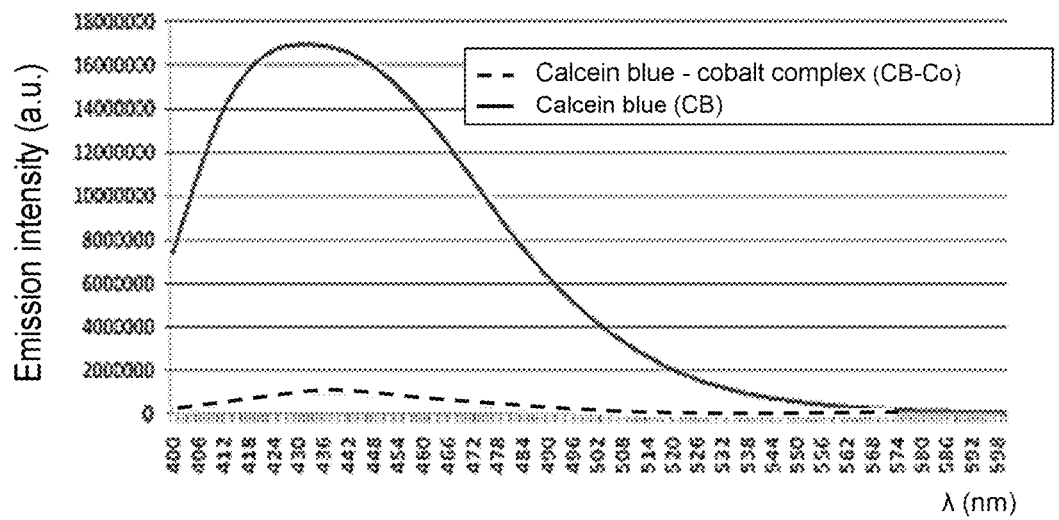

FIG. 6 illustrates the fact that the fluorescence of the calcein blue is quenched after addition of a cobalt ion ($Co^{2+}$). [(wavelength λ in nm/emission intensity in arbitrary units (a.u.)].

Figure 7:
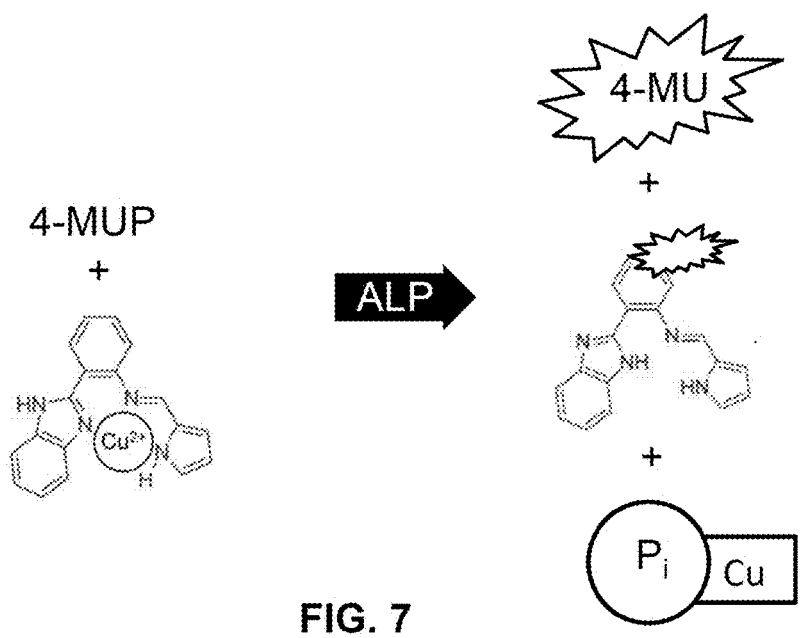

FIG. 7 schematically represents a specific reaction for activating the fluorogenic enzymatic substrate 4-methylumbelliferyl phosphate (4-MUP), optimized by the quenched chemosensor-cation complex of formula (II) associating a benzimidazole derivative with the copper ion ($Cu^{2+}$):

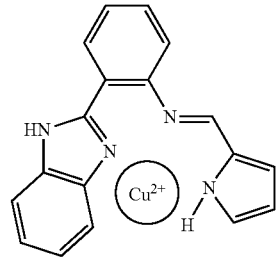

(II)

the substrate 4-MUP being converted by the enzyme alkaline phosphatase (ALP) to give 4-methylumbelliferone (4-MU) and a hydrogen phosphate ion $HPO_4^{2-}$ (Pi represents inorganic phosphate in all its forms), said resultant hydrogen phosphate ion $HPO_4^{2-}$ associating with the cation $Cu^{2+}$ of the quenched chemosensor-cation complex associating a benzimidazole derivative with the copper ion ($Cu^{2+}$), to form on the one hand a non-fluorescent product associating the cation $Cu^{2+}$ with the phosphate ion (Pi-Cu) and on the other hand to release the fluorescent benzimidazole derivative N-[2-(1H-benzo[d]imidazol-2-yl)phenyl]-N-[(E)-1-(1H-pyrrol-2-yl)methylidene]amine of the following formula (I):

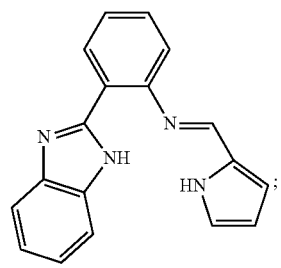

(I)

Figure 8:
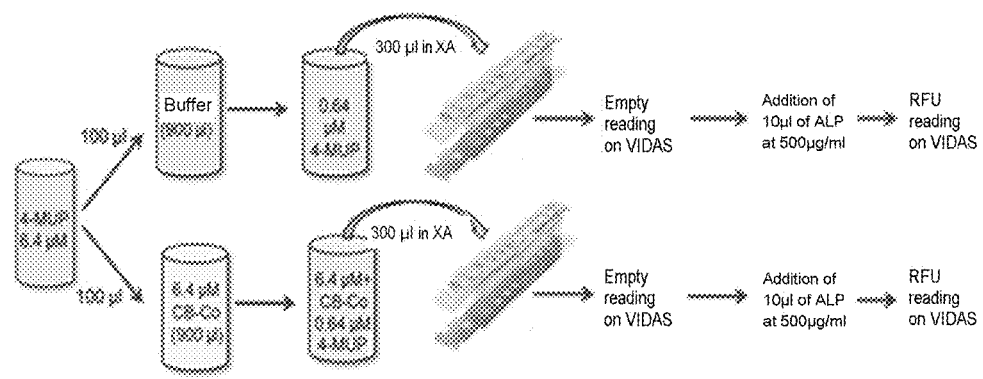
Figure 9:
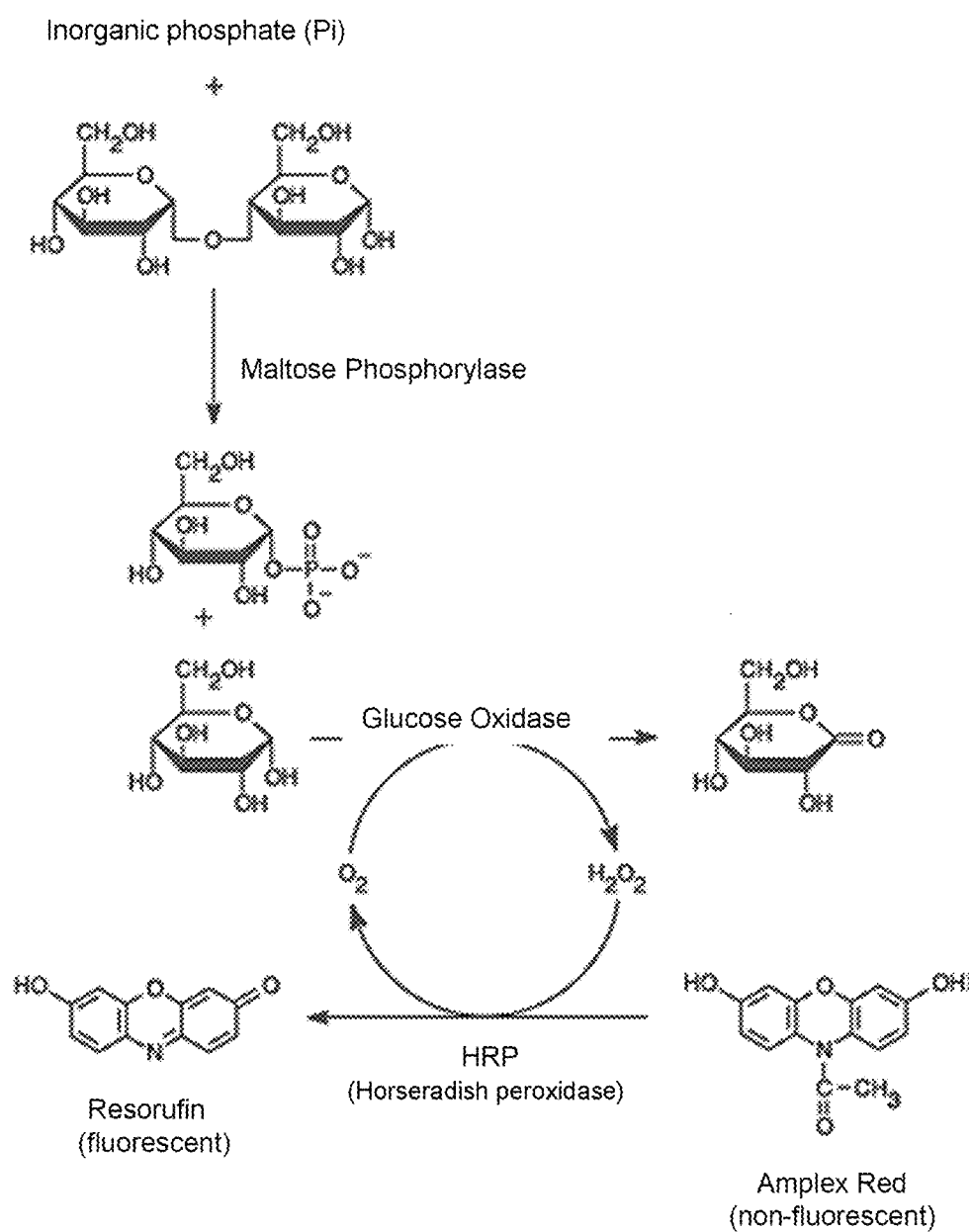
Figure 10:
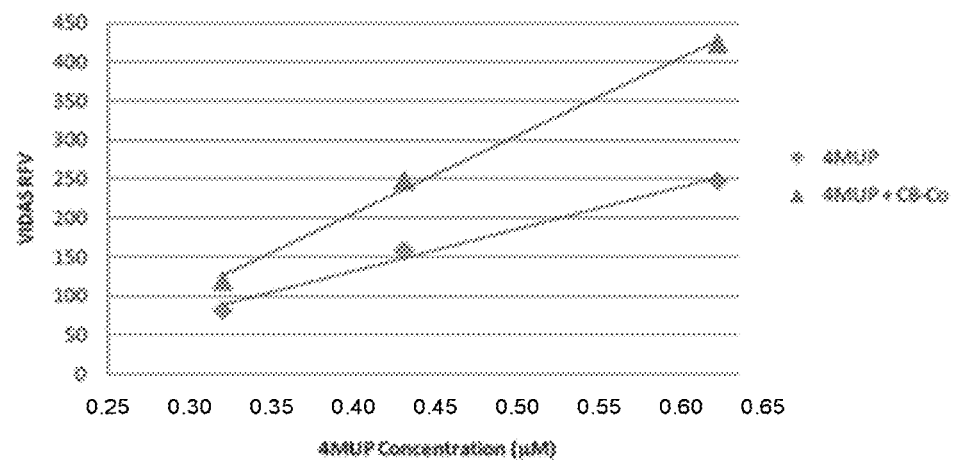
Figure 11:
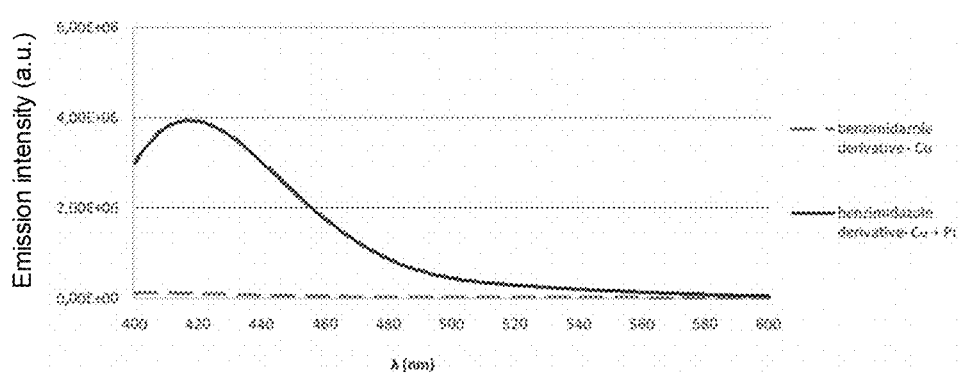

FIG. 8 schematically represents the different steps in a test described in detail in example 3, making it possible especially to determine the additional fluorescence generated by a fluorescent compound according to the invention;

FIG. 9 schematically represents the principle of the PiPer™ [PiPer™ Phosphate Assay kit (Invitrogen™)] assay in which, in the presence of inorganic phosphate, maltose phosphorylase converts maltose into glucose and glucose-1-phosphate. Glucose oxidase then converts glucose into gluconolactone and $H_2O_2$. Finally, with horseradish peroxidase (HRP), $H_2O_2$ reacts with the non-fluorescent reagent Amplex Red to generate the highly fluorescent molecule Resorufin;

FIG. 10 compares the mean fluorescence between on the one hand a composition for enzyme immunoassay using immunofluorescence comprising only one fluorogenic enzymatic substrate which is 4-MUP, and on the other hand a composition for enzyme immunoassay using immunofluorescence according, to the invention, comprising both a fluorogenic enzymatic substrate which is 4-methylumbelliferyl phosphate (4-MUP) and a quenched chemosensor-cation complex associating calcein blue and a cobalt ion ("CB-Co"); and FIG. 11 shows that the quenched chemosensor-cation complex associating N-[2-(1H-benzo[d]imidazol-2-yl)phenyl]-N-[(E)-1-(1H-pyrrol-2-yl)methylidene]-amine with the copper ion ($Cu^{2+}$) does not indeed emit fluorescence, and that fluorescence is obtained after introducing inorganic phosphate Pi into the medium [wavelength λ in nm/emission intensity in arbitrary units (a.u.)].

The invention therefore relates to a composition for enzyme immunoassay using immunofluorescence comprising (i) a fluorogenic enzymatic substrate and also (ii) a quenched fluorogenic compound forming a fluorescent compound after enzymatic hydrolysis of the substrate (i).

More particularly, this composition according to the invention comprises:
- on the one hand (i), a fluorogenic enzymatic substrate enabling, after enzymatic hydrolysis, the formation of a fluorescent product (referred to as first fluorescent product) and of a second reaction product which is preferentially an anion; and
- on the other hand (ii), a quenched fluorogenic compound enabling the formation of a fluorescent compound (referred to as second fluorescent product) by virtue, especially, of the release of the second reaction product, which is preferentially an anion resulting from the enzymatic hydrolysis of the substrate (i).

The fluorogenic enzymatic substrates which may be used for the purposes of the invention, which may be referred to as primary substrates within the context of the invention, are all substrates known to those skilled in the art, giving, after enzymatic hydrolysis, a fluorescent product and a second reaction product which is preferentially an anion.

According to a particular embodiment of the invention, the primary fluorogenic enzymatic substrate is chosen from 4-methylumbelliferyl phosphate (4-MUP), 4-methylumbelliferyl galactoside (4-MUG), 4-methylumbelliferyl sulfate (4-MUS), fluorescein diphosphate (FDP), 6,8-difluoro-4-methylumbelliferyl phosphate (DiFMUP), 9H-(1,3-dichloro-9,9-dimethylacridin-2-one-7-yl) phosphate (DDAO phosphate), 2'-[2-benzothiazole]-6'-hydroxybenzothiazole phosphate, 2-naphthyl phosphate and 2-umbelliferyl phosphate.

In this particular embodiment, the first fluorescent product formed, "S*", is 4-methylumbelliferone (4-MU), and the second reaction product, "B", is an anion or a sugar.

The primary fluorogenic enzymatic substrate is preferably chosen from 4-methylumbelliferyl phosphate (4-MUP), 4-methylumbelliferyl sulfate (4-MUS) and 4-methylumbelliferyl galactoside (4-MUG). Thus, preferably, the second reaction product is an anion chosen from the hydrogen phosphate ion $HPO_4^{2-}$ (or inorganic phosphate, denoted Pi) and the sulfate ion $SO_4^{2-}$, or is a sugar which is galactoside.

The primary fluorogenic enzymatic substrate is more preferably still chosen from 4-methylumbelliferyl phosphate (4-MUP) and 4-methylumbelliferyl sulfate (4-MUS). Thus, preferably, the second reaction product is a hydrogen phosphate ion $HPO_4^{2-}$ (or inorganic phosphate, denoted Pi) or a sulfate ion $SO_4^{2-}$.

More preferentially still, the primary fluorogenic enzymatic substrate is 4-methylumbelliferyl phosphate (4-MUP) and the second reaction product is the hydrogen phosphate anion $HPO_4^{2-}$.

Enzymes enabling the formation of such a first fluorescent product and a second reaction product are also known to those skilled in the art. Among the enzymes available for enzyme immunoassays using immunofluorescence, mention may especially be made of sulfatase, alkaline phosphatase (ALP), acid phosphatase, glucose oxidase (GOx), glucose-6-phosphate dehydrogenase (G6PD) and β-galactosidase (β-gal).

The enzymes enabling the formation of a fluorescent product and of a second reaction product which is an anion are preferentially chosen from sulfatase, acid phosphatase and alkaline phosphatase (ALP).

According to a particular embodiment, the primary fluorogenic enzymatic substrate is 4-methylumbelliferyl phosphate (4-MUP) which enables the formation of 4-methylumbelliferone (4-MU) and of the hydrogen phosphate ion $HPO_4^{2-}$ in the presence of the enzyme ALP.

The first fluorescent product resulting from the enzymatic reaction is preferentially excited at a wavelength of between 250 and 450 nm and emits at a wavelength of between 300 and 600 nm.

Advantageously, the first fluorescent product is excited at a wavelength of between 300 and 400 nm and emits at a wavelength of between 400 and 500 nm.

More advantageously still, the first fluorescent product is excited at a wavelength of between 350 and 380 nm and emits at a wavelength of between 420 and 480 nm.

"Quenched fluorogenic compound", which may be referred to as secondary substrate within the context of the invention, is intended to mean a compound containing a group which, when it comprises this group bound, is incapable of emitting fluorescence ("fluorescence quenching"), but which emits a fluorescent signal when the group is separated from the compound. This may be referred to as a "quenching" group.

As examples of such quenched fluorogenic compounds, mention may be made of derivatives of fluorescent compounds which are customary for those skilled in the art, such as coumarin or resorufin derivatives, which contain groups which prevent the emission of fluorescence. By way of example of such groups, mention may be made of the group —C(O)—CH$_3$ which, if bound to resorufin, quenches the fluorescence of resorufin. A resorufin derivative comprising such a group is the reagent Amplex® Red, the group loss mechanism of which, to produce fluorescent resorufin in the presence of inorganic phosphate (indirect reaction), is described in the P$_i$Per™ Phosphate Assay kit (Invitrogen™) manual and is schematically represented in FIG. 9. The loss of the "quenching" group is generally produced by the action of an enzyme, this enzyme being horseradish peroxidase in the preceding example. These derivatives of fluorescent compounds may generally be fluorogenic enzymatic substrates, different from the primary fluorogenic enzymatic substrate, as long as they form a fluorescent compound (they are said to be activated) in the presence of the second reaction product released by enzymatic hydrolysis of the primary substrate.

Other examples of quenched fluorescent compounds which may be used for the purposes of the invention comprise selective chemosensors associated with a cation, which are quenched in this associated form. They are referred to as quenched chemosensor-cation complexes. As is illustrated in FIG. 2, this secondary substrate of the type selective chemosensor associated with a cation, "A-cat", is able to be directly subsequently activated by the second reaction product generated after enzymatic hydrolysis of the fluorogenic enzymatic substrate, in the case in FIG. 2 the anion "Pi", which will enable an additional signal to be directly generated.

The use of these compounds as quenched fluorogenic compounds has the advantage that the reaction product "B", or "Pi" in FIG. 2, reacts with the cation of the quenched chemosensor-cation complex and enables:

the formation of a complex associating the reaction product with the cation ("Pi-cat" in FIG. 2) on the one hand and the formation of the fluorescent compound ("A*") which makes it possible to produce a second fluorescent signal. The second fluorescent signal does not require the addition of additional compounds to carry out the set of reactions needed to form the compound in fluorescent form, as in the case of conventional derivatives of fluorescent compounds, which constitutes a particular embodiment of the invention.

By way of nonlimiting example of chemosensor which may be used, the following fluorescent compounds may be mentioned:

(i) hydrophilic coumarins, as described by Jung H. S. et al., 2009, Thomas F. and Serratrice G., 1999, and Yao J. et al., 2009, such as:

7-(diethylamino)-2-oxo-N-((pyridin-2-yl)-methyl)-2H-chromene-3-carboxamide:

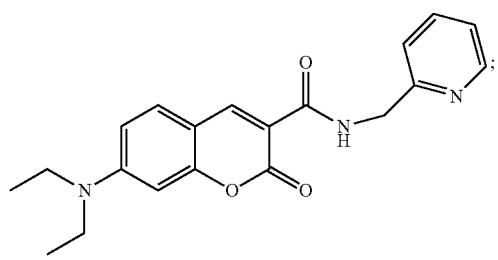 [SMILES: CCN(CC)c1ccc2cc(C(=O)NCc3ccccn3)c(=O)oc2c1]

N-(1,3-dihydroxy-2-(hydroxymethyl)propan-2-yl)-2-oxo-2H-chromene-3-carboxamide:

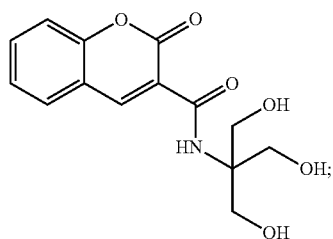 [SMILES: O=C(NC(CO)(CO)CO)c1cc2ccccc2oc1=O]

calcein:

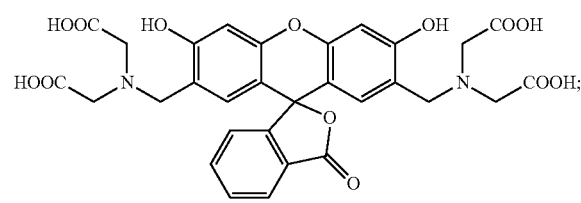 [SMILES: O=C(O)CN(CC(=O)O)Cc1cc2c(cc1O)Oc1cc(O)c(CN(CC(=O)O)CC(=O)O)cc1C21OC(=O)c2ccccc21]

and calcein blue:

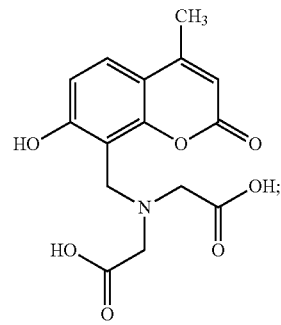 [SMILES: Cc1cc(=O)oc2c(CN(CC(=O)O)CC(=O)O)c(O)ccc12]

(ii) poly(9-aminofluorene), as described in Zhang G. et al., 2012;

(iii) benzimidazole derivatives, as described by Alvaro M. et al., 2001, Henary M. M. et al., 2004 and Saluja P. et al., 2012, such as:

N-[2-(1H-benzo[d]imidazol-2-yl)-phenyl]-N-[(E)-1-(1H-pyrrol-2-yl)methylidene]amine of following formula (I):

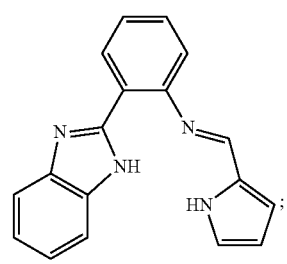

the N,S,-macrocycle of bis-benzimidazole derivative;

{4-[2-(1H-benzimidazol-2-yl)phenyl-sulfamoyl]-phenoxy} acetic acid:

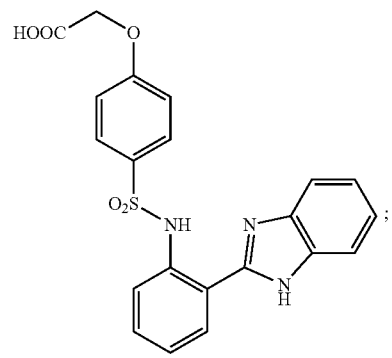 [SMILES: O=C(O)COc1ccc(S(=O)(=O)Nc2ccccc2-c2nc3ccccc3[nH]2)cc1]

{4-{2-{4-[(diethylamino)methyl]-1H-benzimidazol-2-yl}phenyl-sulfamoyl}phenoxy} acetic acid:

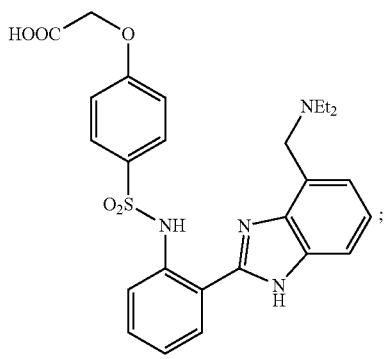

{4-{2-{4-[(methylpyridin-2-ylmethylamino)-methyl]-1H-benzimidazol-2-yl}phenylsulfamoyl}phenoxy} acetic acid:

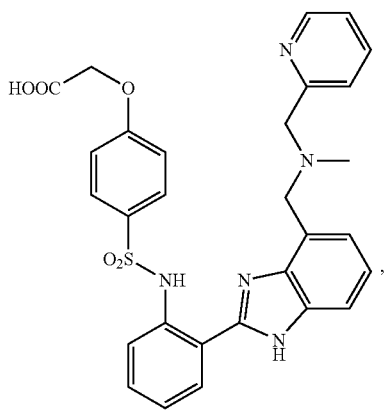 [SMILES: CN(Cc1ccccn1)Cc1cccc2[nH]c(-c3ccccc3NS(=O)(=O)c3ccc(OCC(=O)O)cc3)nc12]

and
{4-{2-{4-[(bispyridin-2-ylmethylamino)methyl]-1H-benzimidazol-2-yl}phenyl sulfamoyl}phenoxy} acetic acid:

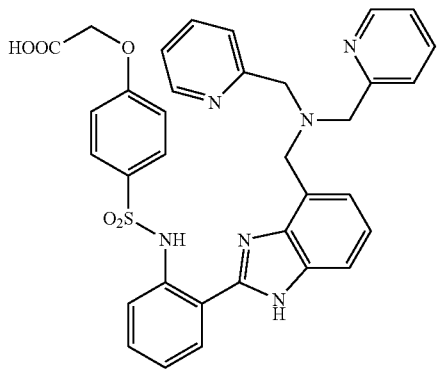 [SMILES: O=C(O)COc1ccc(S(=O)(=O)Nc2ccccc2-c2nc3c(CN(Cc4ccccn4)Cc4ccccn4)cccc3[nH]2)cc1]

The chemosensor used in the composition according to the invention is preferably chosen from hydrophilic coumarins and benzimidazole derivatives.

More preferably still, the chemosensor used in the composition according to the invention is calcein blue or N-[2-(1H-benzo[d]imidazol-2-yl)phenyl]-N-[(E)-1-(1H-pyrrol-2-yl)methylidene]amine.

More preferably still, the chemosensor used in the composition according to the invention is calcein blue.

Said selective chemosensor is associated with a cation to form a quenched chemosensor-cation complex.

The cation is preferably a transition metal, preferably chosen from $Co^{2+}$, $Cr^{3+}$, $Cu^{2+}$, $Fe^{2+}$, $Fe^{3+}$, $Mn^{2+}$, $N^{2+}$, $Hg^{2+}$ and $Pb^{2+}$.

More preferably still, the cation used in the composition according to the invention is $Co^{2+}$ or $Cu^{2+}$.

The quenched chemosensor-cation complex is preferably chosen from:

(i) hydrophilic coumarins quenched by a metal ion, such as the following complexes:
- 7-(diethylamino)-2-oxo-N-((pyridin-2-yl)-methyl)-2H-chromene-3-carboxamide—copper ion ($Cu^{2+}$);
- N-(1,3-dihydroxy-2-(hydroxymethyl)propan-2-yl)-2-oxo-2H-chromene-3-carboxamide—ferric ion ($Fe^{3+}$);
- Calcein—ferric ion ($Fe^{3+}$);
- calcein blue—cobalt ion ($Co^{2+}$);

(ii) water-soluble benzimidazole derivatives quenched by a metal ion, such as the following complexes:
- N-[2-(1H-benzo[d]imidazol-2-yl)-phenyl]-N-[(E)-1-(1H-pyrrol-2-yl)methylidene]amine—copper ion ($Cu^{2+}$), of the following formula (II):

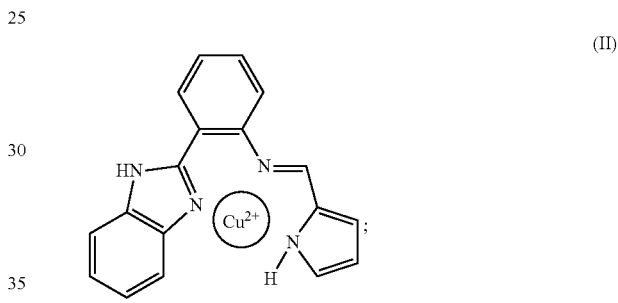

(II)

the N,S,-macrocycle of bis-benzimidazole derivative, quenched by an ion chosen from $Cu^{2+}$, $Fe^{2+}$, $Ni^{2+}$, $Co^{2+}$ and $Mn^{2+}$;

{4-[2-(1H-benzimidazol-2-yl)-phenyl-sulfamoyl]phenoxy} acetic acid, quenched by an ion chosen from $Cu^{2+}$, $Fe^{2+}$, $Ni^{2+}$, $Co^{2+}$ and $Mn^{2+}$;

{4-{2-{4-[(diethylamino)methyl]-1H-benzimidazol-2-yl}phenylsulfamoyl}phenoxy} acetic acid, quenched by an ion chosen from $Cu^{2+}$, $Fe^{2+}$, $Ni^{2+}$, $Co^{2+}$ and $Mn^{2+}$;

{4-{2-{4-[(methylpyridin-2-ylmethylamino)methyl]-1H-benzimidazol-2-yl}phenylsulfamoyl}phenoxy} acetic acid, quenched by an ion chosen from $Cu^{2+}$, $Fe^{2+}$, $Ni^{2+}$, $Co^{2+}$ and $Mn^{2+}$; and {4-{2-{4-[(bispyridin-2-ylmethylamino)methyl]-1H-benzimidazol-2-yl}phenylsulfamoyl}phenoxy} acetic acid, quenched by an ion chosen from $Cu^{2+}$, $Fe^{2+}$, $Ni^{2+}$, $Co^{2+}$ and $Mn^{2+}$.

More preferentially still, the quenched chemosensor-cation complex is chosen from:
- calcein blue—cobalt ion ($Co^{2+}$) and
- N-[2-(1H-benzo[d]imidazol-2-yl)-phenyl]-N-[(E)-1-(1H-pyrrol-2-yl)methylidene]amine—copper ion ($Cu^{2+}$).

Said quenched chemosensor-cation complex enables, after enzymatic reaction, to the formation of a second fluorescent product "A*" which results from the separation of the cation from the fluorescent chemosensor, the cation binding to the anion by ionic bonding.

This second fluorescent product is, like the fluorescent product "S*" resulting from the enzymatic reaction detailed in equation (2), preferentially excited at a wavelength of between 250 and 450 nm and emits at a wavelength of between 300 and 600 nm.

Advantageously, the second fluorescent product is also excited at a wavelength of between 300 and 400 nm and emits at a wavelength of between 400 and 500 nm.

More preferentially still, the first fluorescent product and the second fluorescent product are excited and emit at substantially identical wavelengths.

Saluja P. et al., 2012 disclose the compound N-[2-(1H-benzo[d]imidazol-2-yl)phenyl]-N-[(E)-1-(1H-pyrrol-2-yl)methylidene]amine of the following formula (I):

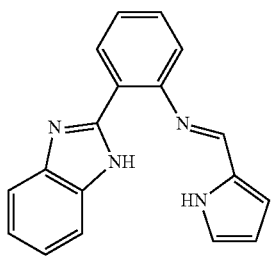

(I)

This compound (I) is fluorescent by default. However, when the compound (I) is associated with a cation such as $Cu^{2+}$, it forms a quenched chemosensor-cation complex of formula (II):

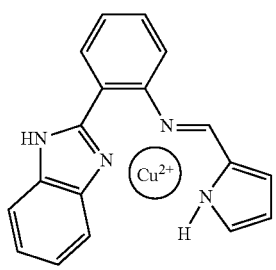

(II)

Finally, the presence of an anion such as inorganic phosphate in the medium will cause the binding of the cation $Cu^{2+}$ to the phosphate ion, releasing the fluorescent compound (I) again.

Particularly advantageously, the composition according to the invention associates a fluorogenic enzymatic substrate which is 4-methylumbelliferyl phosphate (4-MUP) and a quenched chemosensor-ion complex which is the calcein blue-cobalt ion ($Co^{2+}$) complex.

The composition of the invention may also comprise other compounds which may be used in the context of biological assays, such as buffers, for example.

The fluorogenic enzymatic substrate (primary substrate) and the quenched fluorogenic compound (secondary substrate) which are present in the composition of the invention may be contained in a solid medium, for example a solid powder, or in a liquid medium.

"Solid or liquid medium" is intended to denote a medium in solid or liquid form compatible with the sample to be tested which is liable to contain at least one representative analyte to be detected.

The fluorogenic enzymatic substrate and the quenched fluorogenic compound which are present in the composition of the invention are preferably contained in a liquid medium for enzyme immunoassay.

The analyte to be determined may be a protein, a peptide or a hapten, namely a reaction which involves antigens and/or antibodies, receptors for the analyte, etc., as binding partner(s).

The sample to be tested within the context of the invention may be of various origins, for example of food, environmental, biological, veterinary, clinical, pharmaceutical or cosmetic origin.

Among samples of food origin, mention may be made in a non-exhaustive manner of a sample of dairy products (yoghurts, cheeses, etc.), of meat, of fish, of eggs, of fruit, of vegetables, of water, or of beverages (milk, fruit juice, soda, etc.). Of course, these samples of food origin may also originate from sauces or more elaborate dishes or non-transformed or partially transformed starting materials. A food sample may originate from a food intended for animals, such as oil cakes or animal meals. All these samples, if they are not liquid, are treated beforehand to be in liquid form.

As indicated above, the sample may be of environmental origin and may consist, for example, of a surface or water sampling, etc.

The sample may also consist of a biological sample of human or animal origin, which may correspond to samplings of biological fluid (urine, total blood or derivatives such as serum or plasma, saliva, pus, cerebrospinal fluid, etc.), of stools (for example choleraic diarrhea), nose, throat, skin, wound, organ, tissue or isolated cell samplings, or swab samples. This list is of course non-exhaustive.

Generally, the term "sample" refers to a portion or to an amount, more particularly a small portion or a small amount, taken from one or more entities for the purposes of analysis. This sample may have optionally undergone a prior treatment, involving for example steps of mixing, diluting or else milling, in particular if the starting entity is in the solid state.

The sample analyzed is generally liable to contain—or suspected of containing—at least one analyte representative of the presence of microorganisms or of a disease to be detected, characterized or monitored.

Another subject of the invention is a kit for enzyme immunoassay using immunofluorescence of an analyte liable to be contained in a test sample, comprising a composition as defined above.

Of course, the term "immuno" in "immunoassay", for example, is not to be considered in the present application to strictly indicate that the binding partner is an immunological partner such as an antibody. Indeed, those skilled in the art also widely use this term when the binding partner, also referred to as ligand, is not an immunological partner but is, for example, a receptor for the analyte that it is desired to assay. Thus, it is known to refer to ELISA assay ("Enzyme-Linked Immunosorbent Assay") for assays which use non-immunological binding partners, more commonly referred to as "Ligand Binding Assay", while the term "immuno" is included in the acronym ELISA. For the purposes of clarity, the Applicant will use the term "immuno" throughout the application for any assay using a binding partner, even when this is not an immunological partner.

Another subject of the invention is an automated device for immunoanalyses comprising such a composition. An automated device for immunoanalyses is an automated device for biological analyses which makes it possible to carry out a certain number of biological analyses in a limited amount of time. The automated devices for immunoanalyses according to the invention enable, for example, the assay of cardiac markers, thyroid panel, anemia assessment, assay of tumor markers, fertility assessment, viral response, the presence of bacteria or bacteria proteins. By way of nonlimiting examples of automated devices, mention may be made of the following automated devices:

- Access® 2, UniCel™ DxI 600 and UniCel™ DxI 800, sold by Beckman Coulter;
- Advia Centaur™ and Immulite™ sold by Siemens;
- Vitros™ sold by Ortho-Clinical-Diagnostics;
- VIDAS® sold by the Applicant;
- Architect™ sold by Abbott Diagnostics; and
- Elecsys™ sold by Roche Diagnostics.

The automated device is preferably VIDAS®, VIDAS® 3 or miniVIDAS®, sold by the Applicant.

The invention also relates to the use of a composition, of a kit or of an automated device as described above, for the enzyme immunoassay using immunofluorescence of an analyte of interest.

The analysis of samples by enzyme immunoassay employs a reaction between the analyte of interest and one or more binding partner(s) specific to the analyte. These binding partners may be used as capture partner, as detection partner, or as capture and detection partners depending on the assay being used.

By way of binding partner for the analyte, mention may be made of antibodies, fragments of antibodies, nanofitins, receptors for this analyte or any other molecular receptor which is known to interact with the analyte to be researched.

Binding partner antibodies are for example polyclonal antibodies or monoclonal antibodies.

Polyclonal antibodies may be obtained by immunization of an animal with the analyte or an immunogenic portion of the analyte, followed by recovery of the desired antibodies in purified form, by taking the serum of said animal, and separation of said antibodies from the other serum constituents, in particular by affinity chromatography on a column to which an antigen specifically recognized by the antibodies, especially the analyte, is bound.

The monoclonal antibodies can be obtained by means of the hybridoma technology, the general principle of which is recalled below.

Firstly, an animal, generally a mouse, is immunized with the analyte or an immunogenic portion of the analyte of interest, and the B lymphocytes of said mouse are then capable of producing antibodies against this antigen. These antibody-producing lymphocytes are then fused with "immortal" myeloma cells (murine in the example) so as to give rise to hybridomas. The cells capable of producing a particular antibody and of multiplying indefinitely are then selected from the heterogeneous mixture of cells thus obtained. Each hybridoma is multiplied in the form of a clone, each one resulting in the production of a monoclonal antibody in which the properties of recognition with respect to said target analyte may be tested, for example, by ELISA, by one-dimensional or two-dimensional Western blotting, by immunofluorescence, or using a biosensor. The monoclonal antibodies thus selected are subsequently purified, especially according to the affinity chromatography technique described above.

The monoclonal antibodies may also be recombinant antibodies obtained by genetic engineering, using techniques well known to those skilled in the art.

By way of example of antibody fragments, mention may be made of the Fab, Fab', F(ab')2 fragments, and also the scFv (Single chain variable fragment) and dsFv (Double-stranded variable fragment) chains. These functional fragments may especially be obtained by genetic engineering.

Nanofitins (commercial name) are small proteins which, like antibodies, are capable of binding to a biological target, thus making it possible to detect it, to capture it or quite simply to target it within an organism.

The binding partners may be specific or non-specific to the analyte to be detected. They are said to be specific when they are capable of binding exclusively, or virtually exclusively, to these analytes. They are said to be non-specific when the binding selectivity of these analytes is low and when they are thus able to bind to other ligands, such as other proteins or antibodies. According to a preferred embodiment, specific binding partners are used.

The analyte is detected by measuring a signal generated after bringing together the complex formed between the analyte and the binding partners, and the composition according to the invention. The detection is carried out by a method of visualizing a fluorescence, by means of labeling, either of the detection partner directly or indirectly (sandwich method) or of the analyte itself or one or more of the fragments thereof (competitive method).

Labeling is intended to mean attaching an enzyme capable of generating, in the reaction medium, a signal detectable by fluorescence, such as, for example, alkaline phosphatase, after hydrolysis of a suitable fluorogenic enzymatic substrate such as 4-MUP.

The invention also relates to a method for in vitro detection and/or quantification of an analyte by enzyme immunoassay using immunofluorescence of sandwich type in a liquid test sample liable to contain said analyte, comprising the following steps of:

- bringing together a capture partner, attached or not attached beforehand to a solid surface, and said liquid sample for binding the analyte to the capture partner;
- adding a detection partner, which is coupled directly or indirectly to an enzyme capable of lysing the fluorogenic enzymatic substrate of a composition of the invention, for binding to the capture partner-analyte complex;
- bringing together a composition of the invention and the capture partner-analyte-detection partner complex to form a reaction medium; and
- detecting, by immunofluorescence, the presence and/or the amount of analyte by measuring the fluorescence emitted in the reaction medium, that is to say the medium containing the first and second fluorescence products as described above.

Direct or indirect coupling of the enzyme to the detection partner is intended to mean that the enzyme is bound directly to the detection partner recognizing the analyte (direct coupling) or else the enzyme is coupled to a binding partner which recognizes the detection partner which in turn recognizes the analyte (indirect coupling).

Thus, within the context of direct coupling, the complex formed at the end of the assay will consist of:

"Capture partner/analyte/detection partner coupled to the enzyme".

Within the context of indirect coupling, the complex formed at the end of the assay will consist of:

"Capture partner/analyte/detection partner/binding partner coupled to the enzyme". Within the context of the latter embodiment, the binding partner is well known to those skilled in the art and may for example be an anti-IgG (immunoglobulin) antibody, when the detection partner is an IgG recognizing the analyte of interest.

The invention also relates to a method for in vitro detection and/or quantification of an analyte by enzyme immunoassay using immunofluorescence of competitive type in a liquid test sample liable to contain said analyte, comprising the following steps of:

bringing together a capture partner, attached or not attached beforehand to a solid surface, an analog of the analyte coupled to an enzyme able to lyse the fluorogenic enzymatic substrate of a composition of the invention, and said liquid sample, which compete to bind to the capture partner;

bringing together a composition of the invention and the capture partner-analyte and capture partner-analyte analog complexes to form a reaction medium; and detecting, by immunofluorescence, the presence and/or amount of analyte by measuring the fluorescence emitted in the reaction medium, that is to say the medium containing the first and second fluorescence products as described above.

Aside from the use of the composition of the invention, the steps of these methods are conventional steps widely known to those skilled in the art.

Moreover, the methods of the invention may also comprise one or more additional steps of rinsing after each step, such as, for example:

before adding the detection partner, a step of rinsing so as to eliminate the analyte not bound to the capture partner-analyte complex; and after adding the detection partner, a step of rinsing so as to eliminate the unbound detection partner, which constitutes another embodiment of the invention.

The rinsing steps are steps well known to those skilled in the art. They are carried out with buffers which are compatible with the reaction medium and the reading of fluorescence.

Finally, the invention relates to a method for improving the sensitivity of a method for in vitro detection and/or quantification, by enzyme immunoassay using immunofluorescence, of an analyte to be detected in a test sample liable to contain the analyte, characterized in that it comprises the use of a composition or of a kit according to the invention while carrying out the assay.

The present invention will now be illustrated by means of the following examples, which are nonlimiting.

EXAMPLE 1: INCREASING FLUORESCENCE BY ACTIVATING THE FLUOROGENIC ENZYMATIC SUBSTRATE 4-METHYLUMBELLIFERYL PHOSPHATE (4-MUP) COUPLED WITH SELECTIVE DETECTION OF THE INORGANIC PHOSPHATE PI

1. General principles:
1.1. Standard reaction:

As is schematically represented in FIG. 1, the current step of detection by immunofluorescence of the presence of an analyte in the immunoassays carried out in the VIDAS® (bioMerieux) instrument is based on the activation of the fluorogenic enzymatic substrate 4-methylumbelliferyl phosphate (4-MUP) contained in the last vessel (well 10 or XA) of the VIDAS® strip.

In the current configuration, during the last mix of each assay carried out in the VIDAS® instrument, the signal generated by the enzyme alkaline phosphatase (ALP or AP) is proportional to the amount of analyte to be assayed (sandwich method) or inversely proportional to such an amount (competitive method). The enzyme is indirectly bound to the walls of the solid phase receptacle (SPR®) via the formation of the capture partner/analyte/detection partner bound to ALP complex or the capture partner/analyte analog bound to ALP complex, depending on the type of immunoassay chosen, and reacts with the fluorogenic enzymatic substrate 4-methylumbelliferyl phosphate (4-MUP) to generate two products:

4-methylumbelliferone (4-MU) which is a highly fluorescent molecule, the fluorescence of which is measured by the optical scanner of the VIDAS® instrument; and the hydrogen phosphate ion $HPO_4^{2-}$ (or Pi for inorganic phosphate in all its forms) which remains in solution without having a specific role.

FIG. 1 schematically represents this known reaction.

1.2. Improved Reaction:

FIG. 2 schematically represents an improved reaction for detection by immunofluorescence according to the invention. This reaction consists on the one hand of the conventional activation of a fluorogenic enzymatic substrate, which in this case is 4-methylumbelliferyl phosphate (4-MUP). This reaction is moreover optimized by virtue of a quenched chemosensor-cation complex ("A-cat" diamond schematically represented in FIG. 2).

As for the reaction schematically represented in FIG. 1, the primary fluorogenic enzymatic substrate 4-MUP is converted by the enzyme alkaline phosphatase (ALP) into 4-methylumbelliferone (4-MU) and a hydrogen phosphate ion $HPO_4^{2-}$ (Pi for inorganic phosphate in all its forms). This resultant phosphate ion (Pi) reacts with the quenched chemosensor-cation complex (secondary substrate) to release, into the medium, on the one hand the fluorescent compound "A*" and on the other hand to form a product associating the phosphate ion (Pi) with the cation "cat".

Thus, the method proposed here consists in adding a secondary substrate, which is a quenched chemosensor-cation complex, to the first substrate, which in this example is the fluorogenic enzymatic substrate 4-methylumbelliferyl phosphate (4-MUP). This secondary substrate is able to be subsequently activated by an anion, which in this example is inorganic phosphate Pi, and which will make it possible to generate an additional signal (cf. diagram of FIG. 2).

The fluorescent complex formed in this way, which associates the selective chemosensor with the inorganic phosphate, contributes to reinforcing the overall signal generated by the primary reaction of 4-methylumbelliferyl phosphate (4-MUP).

2. Carrying Out the Reaction with the Fluorophore "Calcein Blue":

As is illustrated in FIG. 3, the improved reaction detailed in section 1.2 above was carried out by the Applicant using, as secondary substrate, the complex associating the chemosensor "calcein blue" (CB) quenched by the cobalt cation ($Co^{2+}$).

Calcein blue or 4-methylumbelliferone-8-methyliminodiacetique acid is a compound, the general formula of which is reproduced below:

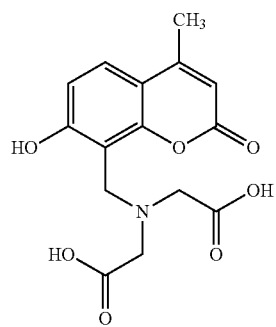

Calcein blue is a coumarin fluorophore which has characteristics similar to 4-methylumbelliferone (4-MU) of the general formula:

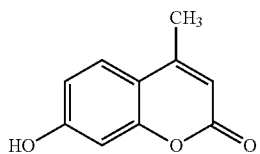

This means that calcein blue is compatible with VIDAS® systems.

The quenched chemosensor-cation complex associating calcein blue and a cobalt ion ("CB-Co") was selected as a potential candidate for the following reasons:
- it is selective for inorganic phosphate Pi;
- as illustrated in FIG. 4, it is well activated by increasing concentrations of inorganic phosphate Pi. Indeed, FIG. 4 illustrates that the quenched chemosensor-cation complex associating calcein blue and a cobalt ion ("CB-Co"), is activated by increasing concentrations of inorganic phosphate Pi and enables the release of fluorescent calcein blue as a function of said concentration of inorganic phosphate Pi;
- it is water soluble;
- it is excited at a wavelength of 370±5 nm and emits at a wavelength of 450±20 nm.
- as illustrated in FIG. 5, it has a fluorescence intensity comparable to 4-methylumbelliferone (4-MU). FIG. 5 compares the emission spectra of the two following solutions comprising calcein blue (CB) in the first case and 4-methylumbelliferone (4-MU) in the second case:
  - a solution at pH 9.4 comprising 6410 nM of calcein blue, 0.6 mM of diethanolamine (DEA); 0.3 mM of ethylenediaminetetraacetic acid (EDTA-$Na_2$) and 0.5 mM of $MgCl_2$; and
  - a VIDAS® OPT solution which comprises 6410 nM (6.4 µM) of fluorogenic enzymatic substrate 4-methyl-umbelliferyl phosphate (4-MUP);
- the bond between calcein blue and the cobalt ion ($Co^{2+}$) is stable at different pHs, including at pH 9.2, corresponding to the pH of VIDAS XA;
- as illustrated in FIG. 6, the chemosensor-cation complex associating calcein blue and a cobalt ion ("CB-Co") is quenched, that is to say that it is not fluorescent before the separation of the cobalt ion ($Co^{2+}$).

Moreover, the Applicant was able to demonstrate that the fluorescence intensity, after separation of the cobalt ion ($Co^{2+}$) remained constant for a period of at least 20 minutes.

EXAMPLE 2: IMPROVING THE FLUORESCENCE EMISSION USING A COMPOSITION ACCORDING TO THE INVENTION

1. Preparation of the Solutions to be Tested

A pH 8.2 buffer was prepared with the following compounds:
Tris-Base+HCl (final pH of 8.2)
0.7 mM [$Mg^{2+}$]
0.03 mM [EDTA-$Na_2$]
0.03 mM [$Co^{2+}$]

Three different solutions were prepared with the addition of the fluorogenic enzymatic substrate 4-methylumbelliferyl phosphate (4-MUP) and/or of the quenched chemosensor-cation complex associating calcein blue and a cobalt ion ("CB-Co"). These were the following solutions A, B and C:
Solution A: 0.64 µM of 4-MUP (free acid form)
Solution B: 6.4 µM of CB-Co
Solution C: 0.64 µM of 4-MUP+6.4 µM of CB-Co 2. Test of Stability of Solutions A and B:

The stability of the solutions A and B was tested by monitoring their fluorescence over time, so as to verify that spontaneous hydrolysis of the fluorogenic enzymatic substrate 4-MUP and the displacement of the cobalt ion ($Co^{2+}$) from the calcein blue CB are prevented.

Tables 1a. and 1b. below give the results in relative fluorescence units (RFU) measured by means of the scanner head of the VIDAS® 3 instrument, obtained by placing three strips filled with solution A and three strips filled with solution B into the instrument.

The results are read using an external portable computer operating the VN

Test Suite SW software which controls the scanner head of the VIDAS® instrument.

TABLE 1a results obtained for solution A (0.64 µM 4-MUP):
Tris-base + HCl 8.2, [Mg] 0.7 mM, [EDTA] 0.03 mM, [Co] 0.03 mM
Solution A (0.64 µM 4-MUP)

| | t 0 (RFU) | t 5 min (RFU) | t 10 min (RFU) | t 15 min (RFU) | t 20 min (RFU) | t 25 min (RFU) | t 30 min (RFU) |
|---|---|---|---|---|---|---|---|
| Strip 1 | 34 | 32 | 33 | 33 | 32 | 33 | 33 |
| Strip 2 | 30 | 29 | 29 | 29 | 29 | 30 | 30 |
| Strip 3 | 33 | 32 | 31 | 31 | 32 | 32 | 32 |

TABLE 1b results obtained for solution B (0.64 µM CB-Co):
Tris-base + HCl 8.2, [Mg] 0.7 mM, [EDTA] 0.03 mM, [Co] 0.03 mM
Solution B (0.64 µM CB-Co)

| | t 0 (RFU) | t 5 min (RFU) | t 10 min (RFU) | t 15 min (RFU) | t 20 min (RFU) | t 25 min (RFU) | t 30 min (RFU) |
|---|---|---|---|---|---|---|---|
| Strip 1 | 34 | 34 | 34 | 34 | 34 | 34 | 33 |
| Strip 2 | 41 | 43 | 43 | 43 | 43 | 43 | 42 |
| Strip 3 | 43 | 44 | 45 | 45 | 44 | 43 | |

The results show that the fluorescence of the compositions remains constant and low. Thus, the two solutions A and B are stable over time, which demonstrates that the fluorogenic enzymatic substrate 4-MUP is not spontaneously hydrolyzed and that the displacement of the cobalt ion ($Co^{2+}$) is avoided.

3. Comparison of the Fluorescences of Solutions a and C:

After this stability test, the following test was carried out three times:
Step 1: Three strips (XA well) were filled with 300 µl of solution A and three strips were filled with solution C. The strips were loaded into the VIDAS® 3 instrument;
Step 2: The background value (BKG) is measured by the scanner head of the VIDAS® instrument at the time t0 for each strip;
Step 3: The enzyme alkaline phosphatase (ALP) is added into each cuvette (10 µl at 500 µg/ml);
Step 4: The fluorescence of each cuvette is measured for a duration of 15 minutes at determined moments;

Step 5: The increase in fluorescence is calculated. The relative fluorescence value (RFV) was determined by subtracting the background value (BKG) from the value of the final reading at t=15 minutes.

A duration of 15 minutes was chosen in order to ensure that the fluorogenic enzymatic substrate 4-MUP contained in solution A is completely activated to give 4-MU.

Moreover, the fluorescence obtained with solution A after 15 minutes is homogeneous with the fluorescence for a 4-methylumbelliferone (4-MU) concentration of 0.6410 µM obtained by diluting 1/10 of a VIDAS® OPT solution (at 6.41 µM) in the same buffer.

The raw results from the test carried out three times are reproduced in tables 2a. and 2b. below:

TABLE 2a results obtained for solution A (0.64 µM 4-MUP)
Tris-base + HCl 8.2, [Mg] 0.7 mM, [EDTA] 0.03 mM, [Co] 0.03 mM
0.64 µM 4-MUP

|  | T0 (RFU) BKG | +AP 10 µl 500 µg/ml | t 5 min (RFV) | t 10 min (RFV) | t 15 min (RFV) |
|---|---|---|---|---|---|
| Strip 1.1 | 45 | 330 | 321 | 318 | 317 |
| Strip 1.2 | 45 | 302 | 295 | 291 | 291 |
| Strip 1.3 | 58 | 258 | 251 | 249 | 250 |
| Strip 2.1 | 46 | 295 | 291 | 289 | 288 |
| Strip 2.2 | 68 | 297 | 282 | 280 | 280 |
| Strip 2.3 | 46 | 291 | 284 | 285 | 286 |
| Strip 3.1 | 45 | 321 | 311 | 309 | 309 |
| Strip 3.2 | 45 | 338 | 330 | 330 | 333 |
| Strip 3.3 | 43 | 329 | 321 | 319 | 319 |

TABLE 2b results obtained for solution C (6.4 µM CB-Co + 0.64 µM 4-MUP)
Tris-base + HCl 8.2, [Mg] 0.7 mM, [EDTA] 0.03 mM, [Co] 0.03 mM
6.4 µM CB-Co + 0.64 µM 4-MUP

|  | T0 (RFU) BKG | +AP 10 µl 500 µg/ml | t 5 min (RFV) | t 10 min (RFV) | t 15 min (RFV) |
|---|---|---|---|---|---|
| Strip 1.1 | 109 | 387 | 463 | 501 | 516 |
| Strip 1.2 | 107 | 381 | 443 | 489 | 513 |
| Strip 1.3 | 110 | 386 | 458 | 503 | 523 |
| Strip 2.1 | 97 | 335 | 404 | 471 | 526 |
| Strip 2.2 | 95 | 333 | 390 | 454 | 525 |
| Strip 2.3 | 95 | 324 | 388 | 426 | 477 |
| Strip 3.1 | 99 | 364 | 460 | 529 | 579 |
| Strip 3.2 | 96 | 378 | 441 | 489 | 529 |
| Strip 3.3 | 94 | 369 | 475 | 524 | 527 |

Finally, table 2c. below reproduces the relative fluorescence values (RFV) for all the tests carried out and the corresponding percentage increases in fluorescence.

TABLE 2c

|  | Solution A (4-MUP) t 15 min - BKG RFV | Solution C (4-MUP + CB-Co) t 15 min - BKG RFV | Increase (%) |
|---|---|---|---|
| Strip 1.1 | 272 | 407 |  |
| Strip 1.2 | 246 | 406 |  |
| Strip 1.3 | 192 | 413 |  |
| Mean RFV test 1 | 237 | 409 | 72% |
| Strip 2.1 | 242 | 429 |  |
| Strip 2.2 | 212 | 430 |  |
| Strip 2.3 | 240 | 382 |  |
| Mean RFV test 2 | 231 | 414 | 79% |
| Strip 3.1 | 264 | 480 |  |
| Strip 3.2 | 288 | 433 |  |
| Strip 3.3 | 276 | 433 |  |
| Mean RFV test 3 | 276 | 449 | 62% |

As detailed in table 2c. above, the mean fluorescence increases by approximately 70% between solution A and solution C which contains the association of the fluorogenic enzymatic substrate 4-MUP and the quenched chemosensor-cation complex CB-Co according to the invention.

Thus, the addition of a quenched chemosensor-cation makes it possible to significantly increase the fluorescent signal.

EXAMPLE 3: USE OF DIFFERENT CONCENTRATIONS OF PRIMARY SUBSTRATE IN A COMPOSITION ACCORDING TO THE INVENTION

Preliminary tests with a quenched chemosensor-cation complex associating calcein blue and a cobalt ion ("CB-Co"):

The Applicant wished to assess the increase in fluorescence by addition of the quenched chemosensor-cation complex CB-Co into a solution comprising different concentrations of fluorogenic enzymatic substrate 4-MUP, compared to a solution comprising just the fluorogenic enzymatic substrate 4-MUP, under the same conditions.

1. Preparation of the Solutions to be Tested

A pH 8.2 buffer was prepared as described in example 2 above.

Three different concentrations of 4-MUP were considered; these are the following concentrations:

(1) 0.64 µM (2) 0.43 µM (3) 0.32 µM.

For each concentration, three different solutions were prepared:

(1) 0.64 µM Concentration:
   Solution A1: 0.64 µM of 4-MUP (free acid form)
   Solution B1: 6.4 µM of CB-Co
   Solution C1: 0.64 µM of 4-MUP+6.4 µM of CB-Co (2) 0.43 µM Concentration:
   Solution A2: 0.43 µM of 4-MUP (free acid form)
   Solution B2: 6.4 µM of CB-Co
   Solution C2: 0.43 µM of 4-MUP+6.4 µM of CB-Co (3) 0.32 µM Concentration:
   Solution A3: 0.32 µM of 4-MUP (free acid form)
   Solution B3: 6.4 µM of CB-Co
   Solution C3: 0.32 µM of 4-MUP+6.4 µM of CB-Co.

2. Experimental Section:

Each experiment was carried out in triplicate and repeated three times, for each concentration of 4-MUP tested. Table 3 below reproduces the loading plan for VIDAS™ for a concentration of 0.64 µM of 4-MUP:

TABLE 3

| Samples | | |
|---|---|---|
| Position 1 | Position 2 | Position 3 |
| Section A | | |
| 6.4 µM CB-Co | empty | empty |
| Section B | | |
| 0.64 µM 4-MUP | 0.64 µM 4-MUP | 0.64 µM 4-MUP |
| Section C | | |
| 0.64 µM 4-MUP + 6.4 µM CB-Co | 0.64 µM 4-MUP + 6.4 µM CB-Co | 0.64 µM 4-MUP + 6.4 µM CB-Co |

Solutions B1, B2 and B3 constitute a control for the stability of the quenched chemosensor-cation complex CB-Co. They make it possible to ensure that the observed increase in fluorescence is indeed linked to the action of the phosphate ion (Pi) i on the Co cation, and not to the chelating action of EDTA on the quenched chemosensor-cation complex CB-Co.

The following tests were each carried out three times (session 1, session 2, session 3) for each concentration of 4-MUP. FIG. 8 summarizes the main steps of the tests carried out. FIG. 8 schematically represents the different steps of the test, making it possible to determine the additional fluorescence generated by a fluorescent compound according to the invention.

The various steps of the test are summarized below:
(i) the plastic of each empty strip is measured using the scanner head of the VIDAS® 3 instrument;
(ii) the strips are filled (XA well) as follows:
  a. Section A→1 strip is filled with 300 µl of solution B (B1, B2 or B3);
  b. Section B→3 strips are filled with 300 µl of solution A (A1, A2 or A3);
  c. Section C→3 strips are filled with 300 µl of solution C (C1, C2 or C3).
(iii) The strips are loaded into a VIDAS® 3 EP VN 1015;
(iv) A background reading (BKG) is taken at T0 for each strip by the same scanner head;
(v) The enzyme alkaline phosphatase (ALP) is added in excess into each cuvette (10 µl at 500 µg/ml);
(vi) The fluorescence of each cuvette is measured every five minutes for fifteen minutes;
(vii) The relative fluorescence value (RFV) is determined by subtracting the background value (T0) from the value of the final reading at t=15 minutes.

The results of the different tests carried out three times at different concentrations of 4-MUP (0.64 µM, 0.43 µM and 0.32 µM) are reproduced in the tables below:

I. Tests During Sessions 1, 2 and 3 for a 4-MUP Concentration of 0.64 µM:

TABLE 4a results obtained for solution A1 (0.64 µM 4-MUP)
0.64 µM 4-MUP

| | T0 (RFU) BKG | +AP 10 µl 500 µg/ml | t 15 min (RFU) |
|---|---|---|---|
| Strip 1.1 | 45 | 330 | 317 |
| Strip 1.2 | 45 | 302 | 291 |
| Strip 1.3 | 58 | 258 | 250 |
| Strip 2.1 | 46 | 295 | 288 |
| Strip 2.2 | 68 | 297 | 280 |
| Strip 2.3 | 46 | 291 | 286 |
| Strip 3.1 | 45 | 321 | 309 |
| Strip 3.2 | 45 | 338 | 333 |
| Strip 3.3 | 43 | 329 | 319 |

TABLE 4b results obtained for solution B1 (6.4 µM CB-Co)
6.4 µM CB-Co

| | T0 (RFU) BKG | T 30 sec (RFU) | t 15 min (RFU) |
|---|---|---|---|
| Strip 1.1 | 68 | 68 | 67 |
| Strip 2.1 | 62 | 64 | 63 |
| Strip 3.1 | 86 | 87 | 86 |

TABLE 4c results obtained for solution C1 (6.4 µM CB-Co + 0.64 µM 4-MUP)
6.4 µM CB-Co + 0.64 µM 4-MUP

| | T0 (RFU) BKG | +AP 10 µl 500 µg/ml | t 15 min (RFU) |
|---|---|---|---|
| Strip 1.1 | 109 | 387 | 516 |
| Strip 1.2 | 107 | 381 | 513 |
| Strip 1.3 | 110 | 386 | 523 |
| Strip 2.1 | 97 | 335 | 526 |
| Strip 2.2 | 95 | 333 | 525 |
| Strip 2.3 | 95 | 324 | 477 |
| Strip 3.1 | 99 | 364 | 579 |
| Strip 3.2 | 96 | 378 | 529 |
| Strip 3.3 | 94 | 369 | 527 |

TABLE 4d

Relative fluorescence values (RFV) for all the tests carried out at a 4-MUP concentration of 0.64 µM.

| | Solution A1 (4-MUP) | Solution C1 (4-MUP + CB-Co) |
|---|---|---|
| | t 15 min - BKG | |
| | RFV | RFV |
| Strip 1.1 | 272 | 407 |
| Strip 1.2 | 246 | 406 |
| Strip 1.3 | 192 | 413 |
| Strip 2.1 | 242 | 429 |
| Strip 2.2 | 212 | 430 |
| Strip 2.3 | 240 | 382 |
| Strip 3.1 | 264 | 480 |
| Strip 3.2 | 288 | 433 |
| Strip 3.3 | 276 | 433 |

II. Tests During Sessions 1, 2 and 3. For a 4-MUP Concentration of 0.43 µM:

TABLE 5a results obtained for solution A2 (0.43 µM 4-MUP)
0.43 µM 4-MUP

|  | T0 (RFU) BKG | +AP 10 µl 500 µg/ml | t 15 min (RFU) |
|---|---|---|---|
| Strip 1.1 | 52 | 218 | 211 |
| Strip 1.2 | 44 | 191 | 184 |
| Strip 1.3 | 44 | 192 | 184 |
| Strip 2.1 | 50 | 224 | 213 |
| Strip 2.2 | 50 | 228 | 217 |
| Strip 2.3 | 57 | 211 | 200 |
| Strip 3.1 | 51 | 227 | 224 |
| Strip 3.2 | 55 | 222 | 219 |
| Strip 3.3 | 52 | 231 | 229 |

TABLE 5b results obtained for solution B2 (6.4 µM CB-Co)
6.4 µM CB-Co

|  | T0 (RFU) BKG | T 30 sec (RFU) | t 15 min (RFU) |
|---|---|---|---|
| Strip 1.1 | 62 | 62 | 61 |
| Strip 2.1 | 61 | 62 | 62 |
| Strip 3.1 | 63 | 61 | 61 |

TABLE 5c results obtained for solution C2 (6.4 µM CB-Co + 0.43 µM 4-MUP)
6.4 µM CB-Co + 0.43 µM 4-MUP

|  | T0 (RFU) BKG | +AP 10 µl 500 µg/ml | t 15 min (RFU) |
|---|---|---|---|
| Strip 1.1 | 76 | 273 | 282 |
| Strip 1.2 | 79 | 260 | 270 |
| Strip 1.3 | 70 | 264 | 275 |
| Strip 2.1 | 86 | 312 | 350 |
| Strip 2.2 | 84 | 316 | 359 |
| Strip 2.3 | 79 | 286 | 328 |
| Strip 3.1 | 78 | 338 | 368 |
| Strip 3.2 | 83 | 344 | 361 |
| Strip 3.3 | 82 | 332 | 362 |

TABLE 5d

Relative fluorescence values (RFV) for all the tests carried out at a 4-MUP concentration of 0.43 µM.

|  | Solution A2 (4-MUP) t 15 min - BKG RFV | Solution C2 (4-MUP + CB-Co) t 15 min - BKG RFV |
|---|---|---|
| Strip 1.1 | 159 | 206 |
| Strip 1.2 | 140 | 191 |
| Strip 1.3 | 140 | 205 |
| Strip 2.1 | 163 | 264 |
| Strip 2.2 | 167 | 275 |
| Strip 2.3 | 143 | 249 |
| Strip 3.1 | 173 | 290 |
| Strip 3.2 | 164 | 278 |
| Strip 3.3 | 177 | 280 |

III. Tests During Sessions 1, 2 and 3 for a 4-MUP Concentration of 0.32 µM:

TABLE 5a results obtained for solution A3 (0.32 µM 4-MUP)
0.32 µM 4-MUP

|  | T0 (RFU) BKG | +AP 10 µl 500 µg/ml | t 15 min (RFU) |
|---|---|---|---|
| Strip 1.1 | 50 | 138 | 134 |
| Strip 1.2 | 60 | 146 | 142 |
| Strip 1.3 | 52 | 139 | 134 |
| Strip 2.1 | 42 | 132 | 129 |
| Strip 2.2 | 48 | 130 | 127 |
| Strip 2.3 | 46 | 137 | 135 |
| Strip 3.1 | 42 | 123 | 121 |
| Strip 3.2 | 47 | 128 | 126 |
| Strip 3.3 | 44 | 123 | 122 |

TABLE 5b results obtained for solution B3 (6.4 µM CB-Co):
6.4 µM CB-Co

|  | T0 (RFU) BKG | T 30 sec (RFU) | t 15 min (RFU) |
|---|---|---|---|
| Strip 1.1 | 56 | 55 | 55 |
| Strip 2.1 | 65 | 65 | 64 |
| Strip 3.1 | 73 | 72 | 71 |

TABLE 5c results obtained for solution C3 (6.4 µM CB-Co + 0.32 µM 4-MUP):
6.4 µM CB-Co + 0.32 µM 4-MUP

|  | T0 (RFU) BKG | +AP 10 µl 500 µg/ml | t 15 min (RFU) |
|---|---|---|---|
| Strip 1.1 | 66 | 165 | 179 |
| Strip 1.2 | 72 | 169 | 183 |
| Strip 1.3 | 65 | 161 | 175 |
| Strip 2.1 | 61 | 184 | 191 |
| Strip 2.2 | 66 | 191 | 200 |
| Strip 2.3 | 67 | 194 | 203 |
| Strip 3.1 | 67 | 167 | 178 |
| Strip 3.2 | 64 | 167 | 180 |
| Strip 3.3 | 68 | 167 | 180 |

TABLE 5d

Relative fluorescence values (RFV) for all the tests carried out at a 4-MUP concentration of 0.32 µM.

|  | Solution A3 (4-MUP) t 15 min - BKG RFV | Solution C3 (4-MUP + CB-Co) t 15 min - BKG RFV |
|---|---|---|
| Strip 1.1 | 84 | 113 |
| Strip 1.2 | 82 | 111 |
| Strip 1.3 | 82 | 110 |
| Strip 2.1 | 87 | 130 |
| Strip 2.2 | 79 | 134 |
| Strip 2.3 | 89 | 136 |
| Strip 3.1 | 79 | 111 |
| Strip 3.2 | 79 | 116 |
| Strip 3.3 | 78 | 112 |

Following these different experiments, the mean RFV values were calculated for each 4-MUP concentration, for each solution A1, A2, A3 and C1, C2 and C3.

These mean values are reproduced in the graph in FIG. 10.

As emerges from FIG. 10, the increase in mean fluorescence between the solutions A (A1, A2, A3) and C (C1, C2, C3) is approximately 50%. This increase in fluorescence is due to the signal generated by the calcein blue.

EXAMPLE 5: PRELIMINARY STABILITY TEST

The stability of the complex CB-Co, of the fluorogenic enzymatic substrate 4-MUP and of the mixture thereof is evaluated by monitoring their fluorescence over time. This is in order to verify that spontaneous hydrolysis of the fluorogenic enzymatic substrate 4-MUP is avoided, as well as the displacement of the cation $Co^{2+}$ from calcein blue (CB).

The results obtained by the Applicant made it possible to demonstrate that there is no spontaneous interaction and that the fluorescence remains stable over time (especially between 0 and 25 minutes).

EXAMPLE 6: USE OF THE N-[2-(1H-BENZO[D]IMIDAZOL-2-YL)PHENYL]-N-[(E)-1-(1H-PYRROL-2-YL)METHYLIDENE]AMINE—COPPER ION ($CU^{2+}$) COMPLEX AS QUENCHED CHEMOSENSOR-CATION COMPLEX

The N-[2-(1H-benzo[d]imidazol-2-yl)-phenyl]-N-[(E)-1-(1H-pyrrol-2-yl)methylidene]amine—copper ion ($Cu^{2+}$) complex of the following formula (II):

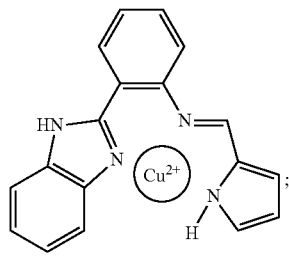

(II)

is another example of chemosensor-cation complex which reacts specifically with inorganic phosphate Pi and which may be used as secondary substrate.

1. Synthesis of N-[2-(1H-benzo[d]imidazol-2-yl)-phenyl]-N-[(E)-1-(1H-pyrrol-2-yl)methylidene]amine The compound N-[2-(1H-benzo[d]imidazol-2-yl)-phenyl]-N-[(E)-1-(1H-pyrrol-2-yl)methylidene]amine is obtained according to the following reaction:

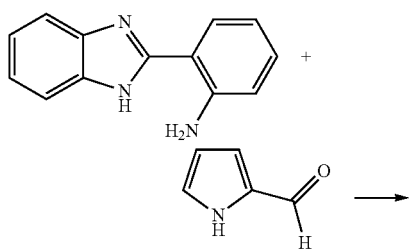

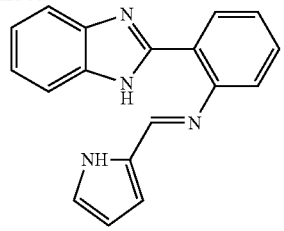

A solution of 2-(2-aminophenyl)-1H-benzimidazole (209 mg, 1.0 mmol) is reacted with pyrrole-2-carboxaldehyde (142 mg, 1.5 mmol) in 50 ml of dry methanol, and heated at reflux for 10 hours. After reaction, the solvent is evaporated to 25 ml and kept at 50° C. for slow evaporation. The white precipitate obtained is then filtered and washed with cold methanol three times.

2. Synthesis of the Chemosensor-Cation Complex:

The N-[2-(1H-benzo[d]imidazol-2-yl)-phenyl]-N-[(E)-1-(1H-pyrrol-2-yl)methylidene]amine—copper ion ($Cu^{2+}$) complex of the following formula (II):

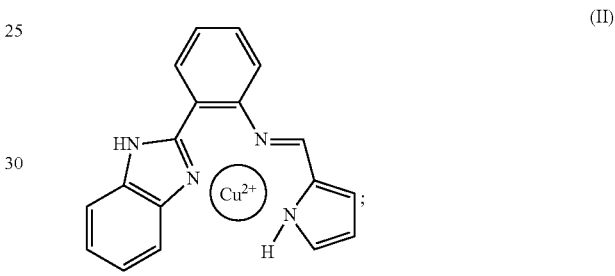

(II)

is obtained by reacting N-[2-(1H-benzo[d]imidazol-2-yl)phenyl]-N-[(E)-1-(1H-pyrrol-2-yl)-methylidene]amine (286 mg, 1.0 mmol) with $Cu(NO_3)_2 \cdot 6H_2O$ (295 mg, 1.0 mmol) in $THF/H_2O$ (30 ml, 1/1, v/v). The mixture is heated at reflux for 8 hours. At the end of the reaction, the product is separated by slow diffusion of diethyl ether in the reaction mixture. The solid obtained is washed in cold methanol and a dark green-colored product is obtained.

3. Activation of the Quenched Chemosensor-Cation Complex:

As illustrated in FIG. 7, this quenched chemosensor-cation complex is activated by inorganic phosphate Pi and makes it possible to form on the one hand a non-fluorescent product associating the cation $Cu^{2+}$ with the hydrogen phosphate ion (Pi-Cu) and on the other hand to release the fluorescent compound [2-(1H-benzo[d]imidazol-2-yl)phenyl]-N-[(E)-1-(1H-pyrrol-2-yl)methylidene]amine. FIG. 11 compares the emission spectrum of a composition comprising the quenched chemosensor-cation complex (N-[2-(1H-benzo[d]imidazol-2-yl)phenyl]-N-[(E)-1-(1H-pyrrol-2-yl)methylidene]amine—copper ion ($Cu^{2+}$)) without inorganic phosphate with the emission spectrum from a composition comprising both the quenched chemosensor-cation complex (N-[2-(1H-benzo[d]imidazol-2-yl)phenyl]-N-[(E)-1-(1H-pyrrol-2-yl)methylidene]amine—copper ion ($Cu^{2+}$)) and inorganic phosphate Pi. As emerges from FIG. 11, the presence of organic phosphate enables the formation on the one hand of the non-fluorescent product associating the cation $Cu^{2+}$ with the hydrogen phosphate ion (Pi-Cu) and on the other hand to release the fluorescent compound [2-(1H-benzo[d]imidazol-2-yl)phenyl]-N-[(E)-1-(1H-pyrrol-2-yl)methylidene]amine.

The fluorescent compound obtained in this way:

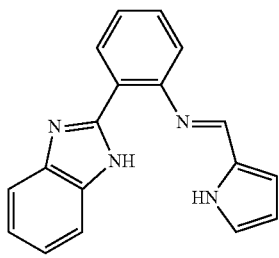 [SMILES: C(=N\c1ccccc1-c1nc2ccccc2[nH]1)/c1ccc[nH]1]

exposed or excited by a source of light of wavelength of approximately 370±5 nm emits light rays or fluorescence signals at a second wavelength of approximately 425±20 nm.

Thus, the fluorescent product is excited and emits at wavelengths which are substantially compatible with 4-methylumbelliferone (4-MU).

This quenched chemosensor-cation complex is also compatible with the pH of VIDAS XA which is approximately 9.2.

LITERATURE REFERENCES

Alvaro M. et al., 2001, Chem. Phys. Lett., 350: 240-246
Henary M. M. et al., 2004, Chem. Eur. J., 10: 3015-3025
Jung H. S. et al., 2009, J. Am. Chem. Soc., 131: 2008-2012
Leong W. L. and Vittal J. J., 2007, Cryst. Growth Des, 7(10): 2112-2116
Rassasie M. J. et al., 1992, Steroids, 57: 112
Saluja P. et al., 2012, Tetrahedron Lett., 53: 3292-3295
Stabler T. V., et al., 1991, Clin. Chem., 37(11): 1987
Thomas F. et al., 1999, J. Biol. Chem., 274: 13375-13383
Yao J. et al, 2009, Inorg. Chem Commun., 12: 116-118
Zhang G. et al., 2012, Sensor Actuat. B-Chem., 171-172: 786-794

The invention claimed is:

1. An enzyme immunoassay system comprising a composition that includes:
a fluorogenic enzymatic substrate that is hydrolysable by an enzyme to produce a first fluorescent reaction product and a second non-fluorescent reaction product; and
a quenched fluorogenic chemosensor-cation complex with which the second non-fluorescent reaction product is reactable to convert the quenched fluorogenic chemosensor-cation complex into an unquenched fluorogenic chemosensor-cation complex,
wherein the fluorogenic enzymatic substrate and quenched fluorogenic chemosensor-cation complex are different compounds.

2. The system as claimed in claim 1, wherein the fluorogenic enzymatic substrate is 4-methylumbelliferyl phosphate (4-MUP), 4-methylumbelliferyl galactoside (4-MUG), 4-methylumbelliferyl sulfate (4-MUS), fluorescein diphosphate (FDP), 6,8-difluoro-4-methylumbelliferyl phosphate (DiFMUP), 9H-(1,3-dichloro-9,9-dimethylacridin-2-one-7-yl) phosphate (DDAO phosphate), 2'-[2-benzothiazole]-6'-hydroxybenzothiazole phosphate, 2-naphthyl phosphate or 2-umbelliferyl phosphate.

3. The system as claimed in claim 1, wherein the fluorogenic enzymatic substrate is 4-methylumbelliferyl phosphate (4-MUP).

4. The system as claimed in claim 1, wherein the chemosensor of the quenched fluorogenic chemosensor-cation complex is selected from the group consisting of hydrophilic coumarins and benzimidazole derivatives, and the cation of the quenched fluorogenic chemosensor-cation complex is selected from the group consisting of $Co^{2+}$, $Cr^{3+}$, $Cu^{2+}$, $Fe^{2+}$, $Fe^{3+}$, $Mn^{2+}$, $Ni^{2+}$, $Hg^{2+}$ and $Pb^{2+}$.

5. The system as claimed in claim 1, wherein the quenched fluorogenic chemosensor-cation complex is calcein blue-cobalt ion ($Co^{2+}$) complex.

6. The system as claimed in claim 1, wherein the quenched fluorogenic chemosensor-cation complex is N-[2-(1H-benzo[d]imidazol-2-yl)-phenyl]-N-RE)-1-(1H-pyrrol-2-yl)methylidene]amine-copper ion ($Cu^{2+}$) complex.

7. The system as claimed in claim 1, wherein the fluorogenic enzymatic substrate is 4-methylumbelliferyl phosphate (4-MUP) and the quenched fluorogenic chemosensor-ion complex is calcein blue-cobalt ion ($Co^{2+}$) complex.

8. An in vitro method for detecting and/or quantifying an analyte when present in a liquid test sample liable to contain the analyte by immunofluorescence using the enzyme immunoassay system as claimed in claim 1, comprising:
bringing together the sample and a capture partner that is attached to a solid surface and binds to the analyte when present in the sample so as to form a capture partner-analyte complex;
binding a detection partner to the capture partner-analyte complex when formed so as to further form a capture partner-analyte-detection partner complex wherein the detection partner is directly or indirectly coupled to an enzyme capable of hydrolyzing the fluorogenic enzymatic substrate;
bringing together (a) the fluorogenic enzymatic substrate and quenched fluorogenic chemosensor-cation complex of the composition and (b) the capture partner-analyte-detection partner complex when formed, so as to form a reaction medium wherein (i) the enzyme hydrolyses the fluorogenic enzymatic substrate to produce the first fluorescent reaction product and the second non-fluorescent reaction product and (ii) the second non-fluorescent reaction product reacts with the quenched fluorogenic chemosensor-cation complex to convert the quenched fluorogenic chemosensor-cation complex into an unquenched fluorogenic chemosensor-cation complex; and
detecting and/or quantifying the analyte when present in the sample by immunofluorescence, which comprises measuring fluorescence emitted from the reaction medium.

9. The method as claimed in claim 8, further comprising at least one of:
eliminating unbound analyte that is not bound within the capture partner-analyte complex by rinsing before binding the detection partner to the capture partner-analyte complex; or
eliminating unbound detection partner that is not bound within the capture partner-analyte-detection partner complex by rinsing after binding of the detection partner to the capture partner-analyte complex.

10. An in vitro method for detecting and/or quantifying an analyte when present in a liquid test sample liable to contain the analyte by immunofluorescence using the enzyme immunoassay system as claimed in claim 1, comprising:
bringing together the sample, an analyte analog, and a capture partner that is attached to a solid surface and binds to the analyte when present in the sample and the analyte analog so as to respectively form a capture partner-analyte complex and capture partner-analyte analog complex wherein the analyte and analyte analog compete to bind with the capture partner, and the analyte analog is coupled to an enzyme capable of hydrolyzing the fluorogenic enzymatic substrate;

bringing together (a) the fluorogenic enzymatic substrate and quenched fluorogenic chemosensor-cation complex of the composition and (b) the capture partner-analyte complex when formed and capture partner-analyte analog complex, so as to form a reaction medium wherein (i) the enzyme coupled to the analyte analog hydrolyses the fluorogenic enzymatic substrate to produce the first fluorescent reaction product and the second non-fluorescent reaction product and (ii) the second non-fluorescent reaction product reacts with the quenched fluorogenic chemosensor-cation complex to convert the quenched fluorogenic chemosensor-cation complex into an unquenched fluorogenic chemosensor-cation complex; and detecting and/or quantifying the analyte when present in the sample by immunofluorescence, which comprises measuring fluorescence emitted from the reaction medium.

11. The method as claimed in claim 10, further comprising:

eliminating any of unbound analyte or unbound analyte analog that is not bound within the capture partner-analyte and capture partner-analyte analog complexes by rinsing before bringing together the fluorogenic enzymatic substrate and quenched fluorogenic chemosensor-cation complex of the composition and the capture partner-analyte and capture partner-analyte analog complexes.

12. The system as claimed in claim 1, wherein the fluorogenic enzymatic substrate has a phosphate or a sulfate group.

13. The system as claimed in claim 1, wherein:

the fluorogenic enzymatic substrate is 4-methylumbelliferyl phosphate (4-MUP), 4-methylumbelliferyl galactoside (4-MUG), 4-methylumbelliferyl sulfate (4-MUS), fluorescein diphosphate (FDP), 6,8-difluoro-4-methylumbelliferyl phosphate (DiFMUP), 9H-(1,3-dichloro-9,9-dimethylacridin-2-one-7-yl) phosphate (DDAO phosphate), 2'-[2-benzothiazole]-6'-hydroxybenzothiazole phosphate, 2-naphthyl phosphate or 2-umbelliferyl phosphate, and the chemosensor of the quenched fluorogenic chemosensor-cation complex is selected from the group consisting of hydrophilic coumarins and benzimidazole derivatives, and the cation of the quenched chemosensor-cation complex is selected from the group consisting of $Co^{2+}$, $Cr^{3+}$, $Cu^{2+}$, $Fe^{2+}$, $Fe^{3+}$, $Mn^{2+}$, $Ni^{2-}$, $Hg^{2+}$ and $Pb^{2+}$.

14. The system as claimed in claim 1, wherein the first fluorescent reaction product and the unquenched fluorogenic chemosensor-cation complex are excited at a first overlapping wavelength range and emit at a second overlapping wavelength range.

15. The system as claimed in claim 14, wherein the first fluorescent reaction product and the unquenched fluorogenic chemosensor-cation complex are excited at a wavelength of between 250 and 450 nm and emit at a wavelength of between 300 and 600 nm.

16. An enzyme immunoassay system comprising a composition that includes:

a fluorogenic enzymatic substrate that is hydrolysable by an enzyme to produce a first fluorescent reaction product and a second non-fluorescent reaction product; and a quenched fluorogenic compound with which the second non-fluorescent reaction product is reactable to convert the quenched fluorogenic compound into an unquenched fluorogenic compound, wherein the fluorogenic enzymatic substrate has a phosphate or a sulfate group, and the fluorogenic enzymatic substrate and quenched fluorogenic compound are different compounds.

17. The system as claimed in claim 16, wherein the first fluorescent reaction product and the unquenched fluorogenic compound are excited at a first overlapping wavelength range and emit at a second overlapping wavelength range.

18. The system as claimed in claim 17, wherein the first fluorescent reaction product and the unquenched fluorogenic compound are excited at a wavelength of between 250 and 450 nm and emit at a wavelength of between 300 and 600 nm.

* * * * *